US006777218B1

(12) United States Patent
Mikkelsen et al.

(10) Patent No.: US 6,777,218 B1
(45) Date of Patent: Aug. 17, 2004

(54) SUBTILASE ENZYMES HAVING AN IMPROVED WASH PERFORMANCE ON EGG STAINS

(75) Inventors: Frank Mikkelsen, Valby (DK); Tina Sejersgård Fanø, Kobenhavn O (DK); Jon E. Ness, Redwood City, CA (US); Mark D. Welch, Fremont, CA (US); Lorraine J. Giver, Sunnyvale, CA (US); Jeremy S. Minshull, Los Altos, CA (US); Torben V. Borchert, Birkeroed (DK); Joel Cherry, Davis, CA (US)

(73) Assignees: Novozymes A/S, Bagsvaerd (DK); Maxygen, Inc, Redwood City, CA (US)

( * ) Notice: Subject to any disclaimer, the term of this patent is extended or adjusted under 35 U.S.C. 154(b) by 0 days.

(21) Appl. No.: 09/533,480

(22) Filed: Mar. 23, 2000

(30) Foreign Application Priority Data

Mar. 14, 2000 (DK) ........................ 2000 00405

(51) Int. Cl.[7] .......................... C12N 9/52; C12N 15/57; C12N 15/74; C11D 3/386
(52) U.S. Cl. ...................... 435/220; 435/69.1; 435/221; 435/252.3; 435/32.01; 435/471; 536/23.2; 510/350
(58) Field of Search ................. 435/220, 221, 435/69.1, 471, 252.35, 320.1; 510/392; 536/23.2

(56) References Cited

U.S. PATENT DOCUMENTS

| | | | | |
|---|---|---|---|---|
| 4,002,572 A | * | 1/1977 | te Nijenhuis | 510/306 |
| 5,208,158 A | * | 5/1993 | Bech et al. | 435/219 |
| 5,217,878 A | * | 6/1993 | van Eekelen et al. | 435/69.1 |
| RE34,606 E | | 5/1994 | Estell et al. | 435/222 |
| 5,324,653 A | * | 6/1994 | van Eekelen et al. | 345/221 |
| 5,336,611 A | * | 8/1994 | van Eekelen et al. | 435/221 |

(List continued on next page.)

FOREIGN PATENT DOCUMENTS

| | | |
|---|---|---|
| EP | 0 130 756 A1 | 1/1985 |
| EP | 0 214 435 A2 | 3/1987 |
| EP | 0 251 446 A2 | 1/1988 |
| EP | 0 260 105 B1 | 3/1988 |
| EP | 0 405 901 A1 * | 1/1991 |
| EP | 0 525 610 A2 | 2/1993 |
| WO | WO 87/04461 | 7/1987 |
| WO | WO 87/05050 | 8/1987 |
| WO | WO 88/08028 | 10/1988 |
| WO | WO 88/08033 | 10/1988 |
| WO | WO 89/06279 | 7/1989 |
| WO | WO 91/00345 | 1/1991 |
| WO | WO 94/02618 | 2/1994 |
| WO | WO 95 10591 | 4/1995 |
| WO | WO 95 10615 | 4/1995 |
| WO | WO 95/27049 | 10/1995 |

(List continued on next page.)

OTHER PUBLICATIONS

Russell et al., Nature, vol. 328, pp. 496–500 (1987).
Thomas et al., Nature, vol. 318, pp. 375–376 (1985).
Russell et al., J. Mol. Biol., vol. 193, pp. 803–813 (1987).

Primary Examiner—Ponnathapu Achutamurthy
Assistant Examiner—William W. Moore
(74) Attorney, Agent, or Firm—Elias J. Lambiris

(57) ABSTRACT

The present invention relates to novel subtilases having an improved wash performance on egg stains. The present invention also relates to isolated nucleic acid sequences encoding the subtilases, nucleic acid constructs, recombinant expression vectors, host cells comprising the nucleic acid construct, and methods for producing and using the subtilases of the invention. Further, the present invention relates to cleaning and detergent compositions comprising the subtilase enzymes of the invention as well as to use of such enzymes in detergent compositions and for removal of egg stains.

25 Claims, 1 Drawing Sheet

```
No:    1        10        20        30        40        50
a)  AQSVPYGVSQIKAPALHSQGYTGSNVKVAVIDSGIDSSHPDLKVAGGASM
b)  AQSVPWGISRVQAPAAHNRGLTGSGVKVAVLDTGI*STHPDLNIRGGASF

No:            60        70        80        90       100
a)  VPSETNPFQDNNSHGTHVAGTVAALNNSIGVLGVAPSASLYAVKVLGADG
b)  VPGEPST*QDGNGHGTHVAGTVAALNNSIGVIGVAPSADLYAVKVLGANG

No:           110       120       130       140       150
a)  SGQYSWIINGIEWAIANNMDVINMSLGGPSGSAALKAAVDKAVASGVVVV
b)  RGSVSGIAQGLEWAAANNMHIANMSLGSDAPSTTLERAVNYATSQGVLVI

No:           160       170       180       190       200
a)  AAAGNEGTSGSSSTVGYPGKYPSVIAVGAVDSSNQRASFSSVGPELDVMA
b)  AATGNNG*SGS***VGYPARYANAMAVGATDQNNRRANFSQYGTGIDIVA

No:           210       220       230       240       250
a)  PGVSIQSTLPGNKYGAYNGTSMASPHVAGAAALILSKHPNWTNTQVRSSL
b)  PGVDIESTYPGSSYDSLSGTSMATPHVAGVAALVKQKNPSWSNVQIRNHL

No:           260       270  275
a)  ENTTTKLGDSFYYGKGLINVQAAAQ
b)  KNTATSLGSTNLYGSGLVNAEAATR
```

U.S. PATENT DOCUMENTS

| | | | |
|---|---|---|---|
| 5,340,735 A | * 8/1994 | Christianson et al. | 435/221 |
| 5,352,603 A | * 10/1994 | Vetter et al. | 435/221 |
| 5,352,604 A | * 10/1994 | Wilson et al. | 435/221 |
| 5,389,307 A | * 2/1995 | Lindegaard et al. | 510/320 |
| 5,453,372 A | * 9/1995 | Vetter et al. | 435/222 |
| 5,482,849 A | * 1/1996 | Branner et al. | 435/222 |
| 5,500,364 A | * 3/1996 | Christianson et al. | 435/221 |
| 5,543,302 A | 8/1996 | Boguslawski et al. | 435/69.1 |
| 5,631,217 A | * 5/1997 | Branner et al. | 510/320 |
| 5,665,587 A | * 9/1997 | Aaslyng et al. | 435/221 |
| 5,677,272 A | * 10/1997 | Ghosh et al. | 510/306 |
| 5,679,630 A | * 10/1997 | Baeck et al. | 510/305 |
| 5,691,295 A | 11/1997 | Maurer et al. | |
| 5,741,694 A | * 4/1998 | Hastrup et al. | 435/222 |
| 5,801,039 A | * 9/1998 | Maurer et al. | 435/221 |
| 5,837,517 A | * 11/1998 | Sierkstra et al. | 435/221 |
| 5,858,757 A | * 1/1999 | van der Osten et al. | 435/221 |
| 5,985,639 A | * 11/1999 | Christianson et al. | 435/221 |
| 6,190,900 B1 | * 2/2001 | Sierkstra et al. | 345/221 |
| 6,197,567 B1 | * 3/2001 | Aaslyng et al. | 435/221 |
| 6,197,589 B1 | * 3/2001 | Maurer et al. | 435/471 |
| 6,271,012 B1 | * 8/2001 | Van Eekelen et al. | 435/221 |
| 6,287,841 B1 | * 9/2001 | Mulleners et al. | 435/221 |
| 6,300,116 B1 | * 10/2001 | van der Osten et al. | 435/220 |

FOREIGN PATENT DOCUMENTS

| | | |
|---|---|---|
| WO | WO 95/29979 | 11/1995 |
| WO | WO 95/30010 | 11/1995 |
| WO | WO 95/30011 | 11/1995 |
| WO | WO 98 55634 | 12/1998 |
| WO | WO 99 20723 | 4/1999 |
| WO | WO 99 27082 | 6/1999 |

* cited by examiner

```
No:   1         10        20        30        40        50
a)    AQSVPYGVSQIKAPALHSQGYTGSNVKVAVIDSGIDSSHPDLKVAGGASM
b)    AQSVPWGISRVQAPAAHNRGLTGSGVKVAVLDTGI*STHPDLNIRGGASF

No:             60        70        80        90        100
a)    VPSETNPFQDNNSHGTHVAGTVAALNNSIGVLGVAPSASLYAVKVLGADG
b)    VPGEPST*QDGNGHGTHVAGTVAALNNSIGVIGVAPSADLYAVKVLGANG

No:             110       120       130       140       150
a)    SGQYSWIINGIEWAIANNMDVINMSLGGPSGSAALKAAVDKAVASGVVVV
b)    RGSVSGIAQGLEWAAANNMHIANMSLGSDAPSTTLERAVNYATSQGVLVI

No:             160       170       180       190       200
a)    AAAGNEGTSGSSSTVGYPGKYPSVIAVGAVDSSNQRASFSSVGPELDVMA
b)    AATGNNG*SGS***VGYPARYANAMAVGATDQNNRRANFSQYGTGIDIVA

No:             210       220       230       240       250
a)    PGVSIQSTLPGNKYGAYNGTSMASPHVAGAAALILSKHPNWTNTQVRSSL
b)    PGVDIESTYPGSSYDSLSGTSMATPHVAGVAALVKQKNPSWSNVQIRNHL

No:             260       270  275
a)    ENTTTKLGDSFYYGKGLINVQAAAQ
b)    KNTATSLGSTNLYGSGLVNAEAATR
```

Fig. 1

SEQUENCE LISTING

```
<160> NUMBER OF SEQ ID NOS: 6

<210> SEQ ID NO 1
<211> LENGTH: 807
<212> TYPE: DNA
<213> ORGANISM: Artificial Sequence
<220> FEATURE:
<223> OTHER INFORMATION: Synthetic
<221> NAME/KEY: CDS
<222> LOCATION: (1)..(807)
<223> OTHER INFORMATION:

<400> SEQUENCE: 1 gcg caa tcg gta cca tgg gga att agc cgt gtg caa gcc cca gct gcc      48
Ala Gln Ser Val Pro Trp Gly Ile Ser Arg Val Gln Ala Pro Ala Ala
1               5                   10                  15
```

-continued

```
cat aac cgt gga ttg aca ggt tct ggt gta aaa gtt gct gtc ctc gat        96
His Asn Arg Gly Leu Thr Gly Ser Gly Val Lys Val Ala Val Leu Asp
         20                  25                  30 aca ggg ata tcc act cat cca gat cta aat att cgt ggt ggc gca agc       144
Thr Gly Ile Ser Thr His Pro Asp Leu Asn Ile Arg Gly Gly Ala Ser
     35                  40                  45 ttt gta cca ggg gaa ccg tcg act caa gat ggg aac ggg cac ggg acg       192
Phe Val Pro Gly Glu Pro Ser Thr Gln Asp Gly Asn Gly His Gly Thr
 50                  55                  60 cac gtt gca gga aca gtg gca gct ctt aat aac tca atc ggt gtg att       240
His Val Ala Gly Thr Val Ala Ala Leu Asn Asn Ser Ile Gly Val Ile
 65                  70                  75                  80 ggt gtg gcg cca agt gct gat cta tac gct gta aaa gta ctt gga gca       288
Gly Val Ala Pro Ser Ala Asp Leu Tyr Ala Val Lys Val Leu Gly Ala
                 85                  90                  95 aat ggt aga gga agc gtt agt gga att gct caa ggt cta gag tgg gct       336
Asn Gly Arg Gly Ser Val Ser Gly Ile Ala Gln Gly Leu Glu Trp Ala
            100                 105                 110 gca gcg aat aac atg cat att gct aac atg agt ctc ggt agt gat gca       384
Ala Ala Asn Asn Met His Ile Ala Asn Met Ser Leu Gly Ser Asp Ala
        115                 120                 125 cct agt act aca ctt gag cgt gca gtc aac tac gcg aca agc cag ggt       432
Pro Ser Thr Thr Leu Glu Arg Ala Val Asn Tyr Ala Thr Ser Gln Gly
    130                 135                 140 gta cta gtt att gca gcg act ggt aac aac ggt tcc ggt tca gta ggc       480
Val Leu Val Ile Ala Ala Thr Gly Asn Asn Gly Ser Gly Ser Val Gly
145                 150                 155                 160 tat cct gct cgt tat gcc aac gca atg gct gta gga gcg act gac caa       528
Tyr Pro Ala Arg Tyr Ala Asn Ala Met Ala Val Gly Ala Thr Asp Gln
                165                 170                 175 aac aac aga cgt gca aac ttt tct cag tac ggt aca gga att gac atc       576
Asn Asn Arg Arg Ala Asn Phe Ser Gln Tyr Gly Thr Gly Ile Asp Ile
            180                 185                 190 gta gca cct ggc gtt gac att gaa agc acc tac cca ggc agc tct tat       624
Val Ala Pro Gly Val Asp Ile Glu Ser Thr Tyr Pro Gly Ser Ser Tyr
        195                 200                 205 gac agc cta agt ggc aca tca atg gct act cca cat gtc gcc ggc gtc       672
Asp Ser Leu Ser Gly Thr Ser Met Ala Thr Pro His Val Ala Gly Val
    210                 215                 220 gcc gca cta gtt aaa caa aag aac cca tct tgg tct aat gta caa att       720
Ala Ala Leu Val Lys Gln Lys Asn Pro Ser Trp Ser Asn Val Gln Ile
225                 230                 235                 240 cga aat cat cta aag aat acg gca act agt tta gga agc acg aac ttg       768
Arg Asn His Leu Lys Asn Thr Ala Thr Ser Leu Gly Ser Thr Asn Leu
                245                 250                 255 tat gga agc gga ctt gtt aac gca gaa gcg gca acg cgt                   807
Tyr Gly Ser Gly Leu Val Asn Ala Glu Ala Ala Thr Arg
            260                 265
```

<210> SEQ ID NO 2
<211> LENGTH: 269
<212> TYPE: PRT
<213> ORGANISM: Artificial Sequence
<220> FEATURE:
<223> OTHER INFORMATION: Synthetic

<400> SEQUENCE: 2

```
Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
```

-continued

```
                   20                  25                  30
    Thr Gly Ile Ser Thr His Pro Asp Leu Asn Ile Arg Gly Gly Ala Ser
            35                  40                  45
    Phe Val Pro Gly Glu Pro Ser Thr Gln Asp Gly Asn Gly His Gly Thr
        50                  55                  60
    His Val Ala Gly Thr Val Ala Ala Leu Asn Asn Ser Ile Gly Val Ile
    65                  70                  75                  80
    Gly Val Ala Pro Ser Ala Asp Leu Tyr Ala Val Lys Val Leu Gly Ala
                    85                  90                  95
    Asn Gly Arg Gly Ser Val Ser Gly Ile Ala Gln Gly Leu Glu Trp Ala
                100                 105                 110
    Ala Ala Asn Asn Met His Ile Ala Asn Met Ser Leu Gly Ser Asp Ala
                115                 120                 125
    Pro Ser Thr Thr Leu Glu Arg Ala Val Asn Tyr Ala Thr Ser Gln Gly
                130                 135                 140
    Val Leu Val Ile Ala Ala Thr Gly Asn Asn Gly Ser Gly Ser Val Gly
    145                 150                 155                 160
    Tyr Pro Ala Arg Tyr Ala Asn Ala Met Ala Val Gly Ala Thr Asp Gln
                    165                 170                 175
    Asn Asn Arg Arg Ala Asn Phe Ser Gln Tyr Gly Thr Gly Ile Asp Ile
                180                 185                 190
    Val Ala Pro Gly Val Asp Ile Glu Ser Thr Tyr Pro Gly Ser Ser Tyr
                195                 200                 205
    Asp Ser Leu Ser Gly Thr Ser Met Ala Thr Pro His Val Ala Gly Val
                210                 215                 220
    Ala Ala Leu Val Lys Gln Lys Asn Pro Ser Trp Ser Asn Val Gln Ile
    225                 230                 235                 240
    Arg Asn His Leu Lys Asn Thr Ala Thr Ser Leu Gly Ser Thr Asn Leu
                    245                 250                 255
    Tyr Gly Ser Gly Leu Val Asn Ala Glu Ala Ala Thr Arg
                260                 265

<210> SEQ ID NO 3
<211> LENGTH: 4
<212> TYPE: PRT
<213> ORGANISM: Artificial Sequence
<220> FEATURE:
<223> OTHER INFORMATION: Synthetic

<400> SEQUENCE: 3

Gly Lys Ala Ser
1

<210> SEQ ID NO 4
<211> LENGTH: 6
<212> TYPE: PRT
<213> ORGANISM: Artificial Sequence
<220> FEATURE:
<223> OTHER INFORMATION: Synthetic

<400> SEQUENCE: 4

Ala Gly Lys Ala Ser Leu
1               5

<210> SEQ ID NO 5
<211> LENGTH: 4
<212> TYPE: PRT
<213> ORGANISM: Artificial Sequence
<220> FEATURE:
```

-continued

<223> OTHER INFORMATION: Synthetic

<400> SEQUENCE: 5

Ala Gly Gly Leu
1

<210> SEQ ID NO 6
<211> LENGTH: 275
<212> TYPE: PRT
<213> ORGANISM: Bacillus

<400> SEQUENCE: 6

Ala Gln Ser Val Pro Tyr Gly Val Ser Gln Ile Lys Ala Pro Ala Leu
1               5                   10                  15

His Ser Gln Gly Tyr Thr Gly Ser Asn Val Lys Val Ala Val Ile Asp
            20                  25                  30

Ser Gly Ile Asp Ser Ser His Pro Asp Leu Lys Val Ala Gly Gly Ala
        35                  40                  45

Ser Met Val Pro Ser Glu Thr Asn Pro Phe Gln Asp Asn Asn Ser His
    50                  55                  60

Gly Thr His Val Ala Gly Thr Val Ala Ala Leu Asn Asn Ser Ile Gly
65                  70                  75                  80

Val Leu Gly Val Ala Pro Ser Ala Ser Leu Tyr Ala Val Lys Val Leu
                85                  90                  95

Gly Ala Asp Gly Ser Gly Gln Tyr Ser Trp Ile Ile Asn Gly Ile Glu
            100                 105                 110

Trp Ala Ile Ala Asn Asn Met Asp Val Ile Asn Met Ser Leu Gly Gly
        115                 120                 125

Pro Ser Gly Ser Ala Ala Leu Lys Ala Ala Val Asp Lys Ala Val Ala
    130                 135                 140

Ser Gly Val Val Val Ala Ala Ala Gly Asn Glu Gly Thr Ser Gly Ser
145                 150                 155                 160

Ser Ser Thr Val Gly Tyr Pro Gly Lys Tyr Pro Ser Val Ile Ala
            165                 170                 175

Val Gly Ala Val Asp Ser Ser Asn Gln Arg Ala Ser Phe Ser Ser Val
                180                 185                 190

Gly Pro Glu Leu Asp Val Met Ala Pro Gly Val Ser Ile Gln Ser Thr
            195                 200                 205

Leu Pro Gly Asn Lys Tyr Gly Ala Tyr Asn Gly Thr Ser Met Ala Ser
    210                 215                 220

Pro His Val Ala Gly Ala Ala Leu Ile Leu Ser Lys His Pro Asn
225                 230                 235                 240

Trp Thr Asn Thr Gln Val Arg Ser Ser Leu Glu Asn Thr Thr Thr Lys
                245                 250                 255

Leu Gly Asp Ser Phe Tyr Tyr Gly Lys Gly Leu Ile Asn Val Gln Ala
            260                 265                 270

Ala Ala Gln
        275

SUBTILASE ENZYMES HAVING AN IMPROVED WASH PERFORMANCE ON EGG STAINS

CROSS-REFERENCE TO RELATED APPLICATIONS

This application claims priority under 35 U.S.C. 119 of Danish application PA 2000 00405 filed on Mar. 14, 2000, the contents of which are fully incorporated herein by reference.

TECHNICAL FIELD

The present invention relates to novel subtilases having an improved wash performance on egg stains. These subtilases are useful exhibiting excellent or improved wash performance on egg stains when used in e.g. cleaning or detergent compositions, such as laundry detergent compositions and dishwash compositions, including automatic dishwash compositions.

The present invention also relates to isolated nucleic acid sequences encoding the subtilases, nucleic acid constructs, recombinant expression vectors, host cells comprising the nucleic acid construct, and methods for producing and using the subtilases of the invention. Further, the present invention relates to cleaning and detergent compositions comprising the subtilase enzymes of the invention as well as to use of such enzymes in detergent compositions and for removal of egg stains.

BACKGROUND OF THE INVENTION

In the detergent industry enzymes have for more than 30 years been implemented in washing formulations. Enzymes used in such formulations comprise proteases, lipases, amylases, cellulases, as well as other enzymes, or mixtures thereof. Commercially most important enzymes are proteases.

An increasing number of commercially used proteases are protein engineered variants of naturally occurring wild type proteases, e.g. DURAZYM® (Novo Nordisk A/S), RELASE® (Novo Nordisk A/S), MAXAPEM® (Gist-Brocades N.V.), PURAFECT® (Genencor International, Inc.).

Further, a number of protease variants are described in the art, such as in EP 130756 (GENENTECH)(corresponding to U.S. Reissue Pat. No. 34,606 (GENENCOR)); EP 214435 (HENKEL); WO 87/04461 (AMGEN); WO 87/05050 (GENEX); EP 260105 (GENENCOR); Thomas, Russell, and Fersht (1985) Nature 318 375–376; Thomas, Russell, and Fersht (1987) J. Mol. Biol. 193 803–813; Russel and Fersht Nature 328 496–500 (1987); WO 88/08028 (Genex); WO 88/08033 (Amgen); WO 95/27049 (SOLVAY S. A.); WO 95/30011 (PROCTER & GAMBLE COMPANY); WO 95/30010 (PROCTER & GAMBLE COMPANY); WO 95/29979 (PROCTER & GAMBLE COMPANY); U.S. Pat. No. 5,543,302 (SOLVAY S. A.); EP 251 446 (GENENCOR); WO 89/06279 (NOVO NORDISK A/S); WO 91/00345 (NOVO NORDISK A/S); EP 525 610 Al (SOLVAY); and WO 94/02618 (GIST-BROCADES N.V.).

However, even though a number of useful proteases and protease variants have been described, there is still a need for new improved proteases or protease variants for a number of industrial uses.

In particular, the problem of removing egg stains from e.g. laundry or hard surfaces has been pronounced due to the fact that many serine proteases are inhibited by substances present in the egg white.

Therefore, an object of the present invention, is to provide improved subtilase enzymes, which are suitable for removal of egg stains from, for example, laundry and/or hard surfaces.

SUMMARY OF THE INVENTION

Thus, in a first aspect the present invention relates to a subtilase enzyme having improved wash performance on egg stains, the subtilase being selected from the group consisting of (a) a subtilase having an amino acid sequence which has at least 88% identity with the amino acid sequence shown as amino acids 1 to 269 of SEQ ID NO:2;

(b) a subtilase which is encoded by a nucleic acid sequence which hybridizes under low stringency conditions with
  (i) a complementary strand of the nucleic acid sequence shown as nucleotides 1 to 807 of SEQ ID NO:1, or
  (ii) a subsequence of (i) of at least 100 nucleotides; and (c) a subtilase encoded by the subtilase encoding part of the nucleic acid sequence cloned into a plasmid fragment present in *Escherichia coli* MT173 DSM 13306, or a variant thereof having at least 88% identity to said subtilase.

In a second aspect the present invention relates to an isolated nucleic acid sequence comprising a nucleic acid sequence which encodes for the subtilases according to the invention.

In a third aspect the present invention relates to an isolated nucleic acid sequence encoding a subtilase, selected from the group consisting of (a) a nucleic acid sequence having at least 88% identity with the nucleic acid sequence shown as nucleotides 1 to 807 SEQ ID NO:1; and (b) a subtilase which is encoded by a nucleic acid sequence which hybridizes under low stringency conditions with
  (i) a complementary strand of the nucleic acid sequence shown as nucleotides 1 to 807 of SEQ ID NO:1, or
  (ii) a subsequence of (i) of at least 100 nucleotides; and (c) the subtilase encoding part of the nucleic acid sequence which has been cloned into a plasmid present in *Escherichia coli* MT173 DSM 13306, or a variant thereof having at least 88% identity to said nucleic acid sequence.

In a fourth aspect the present invention relates to a nucleic acid construct comprising the nucleic acid sequence according to the invention operably linked to one or more control sequences capable of directing the expression of the subtilase in a suitable host.

In a fifth aspect the present invention relates to a recombinant expression vector comprising the nucleic acid construct according to the invention, a promoter, and transcriptional and translational stop signals.

In a sixth aspect the present invention relates to a recombinant host cell comprising the nucleic acid construct of the invention.

In a seventh aspect the present invention relates to a method for producing the subtilase according to the invention, the method comprising:

(a) cultivating a recombinant host cell according to the invention under conditions conducive to the production of the subtilase; and (b) recovering the subtilase.

In an eight aspect the present invention relates to a cleaning or detergent composition, preferably a laundry or dishwash composition, comprising the subtilase according to the invention.

Further aspects of the present invention relate to use of the subtilases according to the invention in a cleaning or detergent composition; use of the subtilases or the compositions according to the invention for removal of egg stains; a method for cleaning or washing, including a method for removal of egg stains from, a hard surface or laundry comprising contacting the hard surface or the laundry with the composition of the invention.

Concerning alignment and numbering reference is made to FIG. 1 which shows alignments between subtilisin BPN' (a) (BASBPN) and the novel subtilase of the invention (b).

These alignments are in this patent application used as a reference for numbering the residues.

DEFINITIONS

Prior to discussing this invention in further detail, the following terms and conventions will first be defined.

| NOMENCLATURE OF AMINO ACIDS | | | | |
|---|---|---|---|---|
| A | = | Ala | = | Alanine |
| V | = | Val | = | Valine |
| L | = | Leu | = | Leucine |
| I | = | Ile | = | Isoleucine |
| P | = | Pro | = | Proline |
| F | = | Phe | = | Phenylalanine |
| W | = | Trp | = | Tryptophan |
| M | = | Met | = | Methionine |
| G | = | Gly | = | Glycine |
| S | = | Ser | = | Serine |
| T | = | Thr | = | Threonine |
| C | = | Cys | = | Cysteine |
| Y | = | Tyr | = | Tyrosine |
| N | = | Asn | = | Asparagine |
| Q | = | Gln | = | Glutamine |
| D | = | Asp | = | Aspartic Acid |
| E | = | Glu | = | Glutamic Acid |
| K | = | Lys | = | Lysine |
| R | = | Arg | = | Arginine |
| H | = | His | = | Histidine |
| X | = | Xaa | = | Any amino acid |

| NOMENCLATURE OF NUCLEIC ACIDS | | |
|---|---|---|
| A | = | Adenine |
| G | = | Guanine |
| C | = | Cytosine |
| T | = | Thymine (only in DNA) |
| U | = | Uracil (only in RNA) |

NOMENCLATURE AND CONVENTIONS FOR DESIGNATION OF VARIANTS

In describing the various subtilase enzyme variants produced or contemplated according to the invention, the following nomenclatures and conventions have been adapted for ease of reference:

A frame of reference is first defined by aligning the isolated or parent enzyme with subtilisin BPN' (BASBPN).

The alignment can be obtained by the GAP routine of the GCG package version 9.1 to number the subtilases using the following parameters: gap creation penalty=8 and gap extension penalty=8 and all other parameters kept at their default values.

Another method is to use known recognized alignments between subtilases, such as the alignment indicated in WO 91/00345. In most cases the differences will not be of any importance.

Such an alignments between subtilisin BPN' (BASBPN) and the novel subtilase of the invention is indicated in FIG. 1.

Thereby a number of deletions and insertions will be defined in relation to BASBPN. In FIG. 1, the novel subtilase according to the invention has 6 deletions in positions 36, 58, 158, 162, 163, and 164 in comparison to BASBPN. These deletions are in FIG. 1 indicated by asterixes (*)

The various modifications performed in a parent enzyme is indicated in general using three elements as follows:

Original Amino Acid Position Substituted Amino Acid

The notation G195E thus means a substitution of a glycine in position 195 with a glutamic acid.

In the case where the original amino acid residue may be any amino acid residue, a short hand notation may at times be used indicating only the position and substituted amino acid:

Position Substituted Amino Acid

Such a notation is particular relevant in connection with modification(s) in homologous subtilases (vide infra).

Similarly when the identity of the substituting amino acid residue(s) is immaterial:

Original Amino Acid Position

When both the original amino acid(s) and substituted amino acid(s) may comprise any amino acid, then only the position is indicated, e.g.: 170.

When the original amino acid(s) and/or substituted amino acid(s) may comprise more than one, but not all amino acid(s), then the selected amino acids are indicated inside brackets:

Original Amino Acid Position {Substituted Amino Acid$_1$, . . . , Substituted Amino Acid$_n$}

For specific variants the specific three or one letter codes are used, including the codes Xaa and X to indicate any amino acid residue.

SUBSTITUTIONS

The substitution of Glutamic acid for glycine in position 195 is designated as:

Gly195Glu or G195E or the substitution of any amino acid residue acid for glycine in position 195 is designated as:

Gly195Xaa or G195X or

Gly195 or G195

The substitution of serine for any amino acid residue in position 170 would thus be designated Xaa170Ser or X170S.

or

170Ser or 170S

Such a notation is particular relevant in connection with modification(s) in homologous subtilases (vide infra). 170Ser is thus meant to comprise e.g. both a Lys170Ser modification in BASBPN and Arg170Ser modification in the subtilase according to the invention (cf. FIG. 1).

For a modification where the original amino acid(s) and/or substituted amino acid(s) may comprise more than one, but not all amino acid(s), the substitution of glycine, alanine, serine or threonine for arginine in position 170 would be indicated by Arg170{Gly,Ala,Ser,Thr} or R170{G,A,S,T} to indicate the variants

R170G, R170A, R170S, and R170T.

DELETIONS

A deletion of glycine in position 195 will be indicated by:

Gly195* or G195*

Correspondingly the deletion of more than one amino acid residue, such as the deletion of glycine and leucine in positions 195 and 196 will be designated Gly195*+Leu196* or G195*+L196*

INSERTIONS

The insertion of an additional amino acid residue such as e.g. a lysine after G195 is indicated by:

Gly195GlyLys or G195GK;

or, when more than one amino acid residue is inserted, such as e.g. a Lys, Ala and Ser after G195 this will be indicated as:

Gly195GlyLysAlaSer or G195GKAS

In such cases the inserted amino acid residue(s) are numbered by the addition of lower case letters to the position number of the amino acid residue preceding the inserted amino acid residue(s). In the above example the sequences 194 to 196 would thus be:

|         | 194 195 196              |
|---------|--------------------------|
| BLSAVI  | A - G - L                |
|         | 194 195 195a 195b 195c 196 |
| Variant | A - G - K - A - S - L    |

In cases where an amino acid residue identical to the existing amino acid residue is inserted it is clear that a degeneracy in the nomenclature arises. If for example a glycine is inserted after the glycine in the above example this would be indicated by G195GG. The same actual change could just as well be indicated as A194AG for the change from

|         | 194 195 196       |
|---------|-------------------|
| BLSAVI  | A - G - L         |
| to      |                   |
|         | 194 195 195a 196  |
| Variant | A - G - G - L     |
|         | 194 194a 195 196  |

Such instances will be apparent to the skilled person, and the indication G195GG and corresponding indications for this type of insertions are thus meant to comprise such equivalent degenerate indications.

FILLING A GAP

Where a deletion in an enzyme exists in the reference comparison with the subtilisin BPN' sequence used for the numbering, an insertion in such a position is indicated as:

*36Asp or *36D for the insertion of an aspartic acid in position 36

MULTIPLE MODIFICATIONS

Variants comprising multiple modifications are separated by pluses, e.g.:

Arg170Tyr+Gly195Glu or R170Y+G195E representing modifications in positions 170 and 195 substituting tyrosine and glutamic acid for arginine and glycine, respectively.

Thus, Tyr167{Gly,Ala,Ser,Thr}+Arg170{Gly,Ala,Ser,Thr} designates the following variants:

Tyr167Gly+Arg170Gly, Tyr167Gly+Arg170Ala,
Tyr167Gly+Arg170Ser, Tyr167Gly+Arg170Thr,
Tyr167Ala+Arg170Gly, Tyr167Ala+Arg170Ala,
Tyr167Ala+Arg170Ser, Tyr167Ala+Arg170Thr,
Tyr167Ser+Arg170Gly, Tyr167Ser+Arg170Ala,
Tyr167Ser+Arg170Ser, Tyr167Ser+Arg170Thr,
Tyr167Thr+Arg170Gly, Tyr167Thr+Arg170Ala,
Tyr167Thr+Arg170Ser, and Tyr167Thr+Arg170Thr.

This nomenclature is particular relevant relating to modifications aimed at substituting, replacing, inserting or deleting amino acid residues having specific common properties, such as residues of positive charge (K, R, H), negative charge (D, E), or conservative amino acid modification(s) of e.g. Tyr167{Gly,Ala,Ser,Thr}+Arg170{Gly,Ala,Ser,Thr}, which signifies substituting a small amino acid for another small amino acid. See section "Detailed description of the invention" for further details.

Proteases

Enzymes cleaving the amide linkages in protein substrates are classified as proteases, or (interchangeably) peptidases (see Walsh, 1979, *Enzymatic Reaction Mechanisms*. W.H. Freeman and Company, San Francisco, Chapter 3).

Numbering of Amino Acid Positions/Residues

If nothing else is mentioned the amino acid numbering used herein correspond to that of the subtilase BPN' (BASBPN) sequence. For further description of the BPN' sequence, see FIG. 1 or Siezen et al., *Protein Engng*. 4 (1991) 719–737.

Serine Proteases

A serine protease is an enzyme which catalyzes the hydrolysis of peptide bonds, and in which there is an essential serine residue at the active site (White, Handler and Smith, 1973 *"Principles of Biochemistry,"* Fifth Edition, McGraw-Hill Book Company, NY, pp. 271–272).

The bacterial serine proteases have molecular weights in the 20,000 to 45,000 Dalton range. They are inhibited by diisopropylfluorophosphate. They hydrolyze simple terminal esters and are similar in activity to eukaryotic chymotrypsin, also a serine protease. A more narrow term, alkaline protease, covering a sub-group, reflects the high pH optimum of some of the serine proteases, from pH 9.0 to 11.0 (for review, see Priest (1977) *Bacteriological Rev*. 41 711–753).

Subtilases

A sub-group of the serine proteases tentatively designated subtilases has been proposed by Siezen et al., *Protein Engng*. 4 (1991) 719–737 and Siezen et al. *Protein Science* 6 (1997) 501–523. They are defined by homology analysis of more than 170 amino acid sequences of serine proteases previously referred to as subtilisin-like proteases. A subtilisin was previously often defined as a serine protease produced by Gram-positive bacteria or fungi, and according to Siezen et al. now is a subgroup of the subtilases. A wide variety of subtilases have been identified, and the amino acid sequence of a number of subtilases has been determined. For a more detailed description of such subtilases and their amino acid sequences reference is made to Siezen et al. (1997).

One subgroup of the subtilases, I-S1 or "true" subtilisins, comprises the "classical", subtilisins, such as subtilisin 168 (BSS168), subtilisin BPN', subtilisin Carlsberg (ALCALASE®, NOVO NORDISK A/S), and subtilisin DY (BSSDY).

A further subgroup of the subtilases, I-S2 or high alkaline subtilisins, is recognized by Siezen et al. (supra). Sub-group I-S2 proteases are described as highly alkaline subtilisins and comprises enzymes such as subtilisin PB92 (BAALKP) (MAXACAL®, Gist-Brocades NV), subtilisin 309 (SAVINASE®, NOVO NORDISK A/S), subtilisin 147 (BLS147) (ESPERASE®, NOVO NORDISK A/S), and alkaline elastase YaB (BSEYAB).

Parent Subtilase

The term "parent subtilase" describes a subtilase defined according to Siezen et al. (1991 and 1997). For further details see description of "SUBTILASES" immediately above. A parent subtilase may also be a subtilase isolated from a natural source, wherein subsequent modifications have been made while retaining the characteristic of a subtilase. Furthermore, a parent subtilase may also be a subtilase which has been prepared by the DNA shuffling technique, such as described by J. E. Ness et al., Nature Biotechnology, 17, 893–896 (1999). Alternatively the term "parent subtilase" may be termed "wild type subtilase".

Modification(s) of a Subtilase

The term "modification(s)" used herein is defined to include chemical modification of a subtilase as well as genetic manipulation of the DNA encoding a subtilase. The modification(s) can be replacement(s) of the amino acid side chain(s), substitution(s), deletion(s) and/or insertions in or at the amino acid(s) of interest.

Subtilase Variant

In the context of this invention, the term subtilase variant or mutated subtilase means a subtilase that has been produced by an organism which is expressing a mutant gene derived from a parent microorganism which possessed an original or parent gene and which produced a corresponding parent enzyme, the parent gene having been mutated in order to produce the mutant gene from which said mutated subtilase protease is produced when expressed in a suitable host. Analogously, the mutant gene may also be derived from a parent gene produced by DNA shuffling technique.

Homologous Subtilase Sequences

In the present context the homology between two amino acid sequences is described by the parameter "identity".

In order to determine the degree of identity between two subtilases the GAP routine of the GCG package version 9.1 can be applied (infra) using the same settings. The output from the routine is besides the amino acid alignment the calculation of the "Percent Identity" between the two sequences.

Based on this description it is routine for a person skilled in the art to identify suitable homologous subtilases and corresponding homologous active site loop regions, which can be modified according to the invention.

Isolated Nucleic Acid Sequence

The term "isolated nucleic acid sequence" as used herein refers to a nucleic acid sequence, which has been isolated and purified and is thus in a form suitable for use within genetically engineered protein production systems. Such isolated molecules may be those that are separated from their natural environment and include cDNA and genomic clones as well as nucleic acid sequences derived from DNA shuffling experiments or from site-directed mutagenisis experiments. Isolated nucleic acid sequences of the present invention are free of other genes with which they are ordinarily associated, but may include 5' and 3' untranslated regions such as promoters and terminators. The identification of associated regions will be evident to one of ordinary skill in the art (see for example, Dynan and Tijan, Nature 316:774–78, 1985). The term "isolated nucleic acid sequence" may alternatively be termed "isolated DNA sequence, "cloned nucleic acid sequence" or "cloned DNA sequence".

Isolated Protein

When applied to a protein, the term "isolated" indicates that the protein has been removed from its native environment.

In a preferred form, the isolated protein is substantially free of other proteins, particularly other homologous proteins (i.e. "homologous impurities" (see below)).

An isolated protein is more than 10% pure, preferably more than 20% pure, more preferably more than 30% pure, as determined by SDS-PAGE. Further it is preferred to provide the protein in a highly purified form, i.e., more than 40% pure, more than 60% pure, more than 80% pure, more preferably more than 95% pure, and most preferably more than 99% pure, as determined by SDS-PAGE.

The term "isolated protein" may alternatively be termed "purified protein".

Homologous Impurities

The term "homologous impurities" means any impurity (e.g. another polypeptide than the subtilase of the invention), which originate from the homologous cell where the subtilase of the invention is originally obtained from.

Obtained From

The term "obtained from" as used herein in connection with a specific microbial source, means that the polynucleotide and/or subtilase produced by the specific source, or by a cell in which a gene from the source has been inserted.

Substrate

The term "substrate" used in connection with a substrate for a protease should be interpreted in its broadest form as comprising a compound containing at least one peptide bond susceptible to hydrolysis by a subtilisin protease.

Product

The term "product" used in connection with a product derived from a protease enzymatic reaction should, in the context of the present invention, be interpreted to include the products of a hydrolysis reaction involving a subtilase protease. A product may be the substrate in a subsequent hydrolysis reaction.

Wash Performance

In the present context the term "wash performance" is used as an enzyme's ability to remove egg stains present on the object to the cleaned during e.g. wash or hard surface cleaning. See also the "Model Detergent Wash Performance Test" in Example 2, herein.

Performance Factor

The term "Performance Factor" is defined with respect to the below formula $$P = R_{subtilase} - R_{savinase}$$

wherein P is the Performance Factor, $R_{subtilase}$ is the reflectance of the test material after being treated with a subtilase enzyme of the invention as described in the "Model Detergent Wash Performance Test", and $R_{savinase}$ is the reflectance of the test material after being treated with Savinase® as described in the "Model Detergent Wash Performance Test". For further details, see the "Model Detergent Wash Performance Test" in Example 2, herein.

BRIEF DESCRIPTION OF THE DRAWING

FIG. 1 shows an alignment between subtilisin BPN' (a) and the amino acid sequence of the novel subtilase of the invention (b) using the GAP routine mentioned above.

DETAILED DESCRIPTION OF THE INVENTION

In a first interesting aspect of the present invention, the subtilase enzyme having improved wash performance on egg stains is an isolated subtilase which has at least 88% identity with the amino acid sequence shown as amino acids 1 to 269 of SEQ ID NO:2 (i.e. the mature subtilase). In an interesting embodiment of the invention the subtilase has at least 90%, at least 91%, at least 92%, at least 93%, at least 94%, at least 95%, at least 96%, at least 97%, at least 98%, or at least 99% identity with the amino acid sequence shown as amino acids 1 to 269 of SEQ ID NO:2 (hereinafter "homologous subtilases"). In another interesting embodiment of the invention the isolated subtilase consists of the amino acid sequence shown as amino acids 1 to 269 of SEQ ID NO:2.

Alignments of sequences and calculation of identity scores can be done using a full Smith-Waterman alignment, useful for both protein and DNA alignments. The default scoring matrices BLOSUM50 and the identity matrix are used for protein and DNA alignments respectively. The penalty for the first residue in a gap is -12 for proteins and -16 for DNA, while the penalty for additional residues in a gap is -2 for proteins and -4 for DNA. Align is from the fasta package version v20u6 (W. R. Pearson and D. J. Lipman (1988), "Improved Tools for Biological Sequence Analysis", PNAS 85:2444–2448, and W. R. Pearson (1990) "Rapid and Sensitive Sequence Comparison with FASTP and FASTA" Methods in Enzymology 183:63–98).

By performing such alignments, the following identities (in percentage) between the amino acid sequences of the subtilase having the amino acid sequence of SEQ ID NO:2 and various known subtilases were found:

|  | BLSAVI | BLAP | BASBPN | BLSCAR | SEQ ID NO:2 |
|---|---|---|---|---|---|
| BLSAVI | 100 | | | | |
| BLAP[1] | 98.1 | 100 | | | |
| BASBPN | 60.4 | 60.7 | 100 | | |
| BLSCAR | 60.9 | 61.3 | 69.5 | 100 | |
| SEQ ID NO:2 | 86.6 | 87.4 | 59.3 | 55.8 | 100 |

[1](Bacillus lentus Alkaline Protease) has been described in U.S. Pat. No. 5,352,604

In another interesting embodiment of the invention the isolated subtilase is encoded by a nucleic acid sequence which hybridizes under low stringency conditions, preferably under medium stringency conditions, more preferably under high stringency conditions with (i) a complementary strand of the nucleic acid sequence shown as nucleotides 1 to 807 of SEQ ID NO:1, or (ii) a subsequence of (i) of at least 100 nucleotides (J. Sambrook, E. F. Fritsch, and T. Maniatus, 1989, Molecular Cloning, A Laboratory Manual, 2d edition, Cold Spring Harbor, N.Y.).

The subsequence of the complementary strand of the nucleic acid sequence shown as nucleotidesl to 807 of SEQ ID NO:1 may be at least 100 nucleotides or preferably at least 200 nucleotides. Moreover, the subsequence should encode a subtilase fragment which has proteolytic activity. The subtilases may also be allelic variants or fragments of the subtilases that have proteolytic activity.

The nucleic acid sequence of SEQ ID NO:1 or a subsequence thereof, as well as the amino acid sequence of SEQ ID NO:2 or a fragment thereof, may be used to design a nucleic acid probe to identify and clone DNA encoding subtilases having proteolytic activity from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 15, preferably at least 25, and more preferably at least 35 nucleotides in length. Longer probes can also be used. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

Thus, a genomic DNA or cDNA library prepared from such other organisms may be screened for DNA which hybridizes with the probes described above and which encodes a subtilase according to the invention. Genomic or other DNA from such other organisms may be separated by agarose or polyacrylamide gel electrophoresis, or other separation techniques known by the skilled person. DNA from the libraries or the separated DNA may be transferred to and immobilized on nitrocellulose or other suitable carrier materials. In order to identify a clone or DNA which is homologous with SEQ ID NO:1 or a subsequence thereof, the carrier material is used in a Southern blot. For purposes of the present invention, hybridization indicates that the nucleic acid sequence hybridizes to a labeled nucleic acid probe corresponding to the nucleic acid sequence shown in SEQ ID NO:1, its complementary strand, or a subsequence thereof, under low to high stringency conditions. Molecules to which the nucleic acid probe hybridizes under these conditions are detected using X-ray film.

For long probes of at least 100 nucleotides in length, low to high stringency conditions are defined as prehybridization and hybridization at 42° C. in 5×SSPE, 0.3% SDS, 200

μg/ml sheared and denatured salmon sperm DNA, and either 25% formamide for low stringency, 35% formamide for medium stringency, or 50% formamide for high stringency, following standard Southern blotting procedures.

For long probes of at least 100 nucleotides in length, the carrier material is finally washed three times each for 15 minutes using 2×SSC, 0.2% SDS preferably at least at 50° C. (low stringency), more preferably at least at 55° C. (medium stringency), even more preferably at least at 65° C. (high stringency). For short probes, which are about 15 nucleotides to about 70 nucleotides in length, stringency conditions are defined as prehybridization, hybridization, and washing post-hybridization at 5° C. to 10° C. below the calculated $T_m$ using the calculation according to Bolton and McCarthy (1962, Proceedings of the National Academy of Sciences USA 48:1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml, following standard Southern blotting procedures.

For short probes, which are about 15 nucleotides to about 70 nucleotides in length, the carrier material is washed once in 6×SCC plus 0.1% SDS for 15 minutes and twice each for 15 minutes using 6×SSC at 5° C. to 10° C. below the calculated $T_m$.

It is well known in the art that a so-called conservative substitution of one amino acid residue to a similar amino acid residue is expected to produce only a minor change in the characteristic of the enzyme.

Table I below list groups of conservative amino acid substitutions.

TABLE I

| Conservative amino acid substitutions | |
|---|---|
| Common Property | Amino Acid |
| Basic (positive charge) | K = lysine |
| | H = histidine |
| Acidic (negative charge) | E = glutamic acid |
| | D = aspartic acid |
| Polar | Q = glutamine |
| | N = asparagine |
| Hydrophobic | L = leucine |
| | I = isoleucine |
| | V = valine |
| | M = methionines |
| Aromatic | F = phenylalanine |
| | W = tryptophan |
| | Y = tyrosine |
| Small | G = glycine |
| | A = alanine |
| | S = serine |
| | T = threonine |

Therefore, in a further interesting embodiment of the invention, the subtilase having the amino acid sequence of SEQ ID NO:2 is combined with a substitution, deletion and/or insertion of one or more amino acid residues.

Especially, combinations with other modifications known in the art to provide improved properties to the enzyme are envisaged. The art describes a number of subtilase variants with different improved properties and a number of those are mentioned in the "Background of the invention" section herein (vide supra). Thus, modification of the amino acid sequence SEQ ID NO:2 in one or more of the following positions are contemplated as being of particular relevance (in BASBPN numbering):

27, 36, 56, 76, 87, 97, 101, 104, 120, 123, 167, 170, 222, 224, 235 and 274

In particular, the following variants of the subtilase of the invention are considered appropriate for combination (in BASBPN numbering):

K27R, *36D, S56P, N76D, S87N, G97N, R101G, S103A, V104A, V104I, V104N, V104Y, H120D, N123S, Y167, R170, M222S, M222A, T224S, K235L and T274A.

Furthermore, it is contemplated that insertion of at least one additional amino acid residue in the active site (b) loop region, corresponding to insertion of at least one additional amino acid residue from position 95 to position 103 (BASBPN numbering), will confer additional wash performance to the subtilase of the invention. In particular, it is preferred to insert at least one additional amino acid residue, such as one additional amino acid residue, in the following positions: between positions 98 and 99, and between positions 99 and 100.

Moreover, subtilases which are also considered as being within the scope of the present invention, are isolated subtilases, preferably in a purified form, having immunochemical identity or partial immunochemical identity to the subtilase having the amino acid sequence of SEQ ID NO:2. The immunochemical properties are determined by immunological cross-reaction identity tests by the well-known Ouchterlony double immunodiffusion procedure. Specifically, an antiserum containing polyclonal antibodies which are immunoreactive or bind to epitopes of the subtilase having the amino acid sequence of SEQ ID NO:2 are prepared by immunizing rabbits (or other rodents) according to the procedure described by Harboe and Ingild, In N. H. Axelsen, J. Krøll, and B. Weeks, editors, *A Manual of Quantitative Immunoelectrophoresis*, Blackwell Scientific Publications, 1973, Chapter 23, or Johnstone and Thorpe, *Immunochemistry in Practice*, Blackwell Scientific Publications, 1982 (more specifically pages 27–31). A subtilase having immunochemical identity is a subtilase, which reacts with the antiserum in an identical fashion such as total fusion of precipitates, identical precipitate morphology, and/or identical electrophoretic mobility using a specific immunochemical technique. A further explanation of immunochemical identity is described by Axelsen, Bock, and Krøll, In N. H. Axelsen, J. Krøll, and B. Weeks, editors, *A Manual of Quantitative Immunoelectrophoresis*, Blackwell Scientific Publications, 1973, Chapter 10. A subtilase having partial immunochemical identity is a subtilase, which reacts with the antiserum in a partially identical fashion such as partial fusion of precipitates, partially identical precipitate morphology, and/or partially identical electrophoretic mobility using a specific immunochemical technique. A further explanation of partial immunochemical identity is described by Bock and Axelsen, In N. H. Axelsen, J. Krøll, and B. Weeks, editors, *A Manual of Quantitative Immunoelectrophoresis*, Blackwell Scientific Publications, 1973, Chapter 11.

The antibody may also be a monoclonal antibody. Monoclonal antibodies may be prepared and used, e.g., according to the methods of E. Harlow and D. Lane, editors, 1988, *Antibodies, A Laboratory Manual*, Cold Spring Harbor Press, Cold Spring Harbor, N.Y.

The present inventors have isolated the gene encoding the subtilase having the amino acid sequence shown in SEQ ID NO:2 and inserted it into *E. coli* MT173. The *E. coli* MT173 strain harboring the gene was deposited according to the Budapest Treaty on the International Recognition of the Deposits of Microorganisms for the Purpose of Patent Procedures on Feb. 10, 2000 at the Deutsche Sammlung von Mikroorganismen und Zelikulturen GmbH, Mascheroder Weg 1 B, D-38124 Braunschweig, Germany, and designated the accession No. DSM 13306.

In an interesting embodiment of the invention the subtilase has at least 90%, at least 91%, at least 92%, at least 93%, at least 94%, at least 95%, at least 96%, at least 97%, at least 98%, or at least 99% identity with the subtilase encoded by the subtilase encoding part of the nucleic acid sequence cloned into a plasmid fragment present in E. coli MT173 deposited under the accession No. DSM 13306.

As mentioned above, the subtilase of the invention exhibits excellent wash performance on egg stains. Therefore, in order to enable the skilled person—at an early stage of his development work—to select effective and preferred subtilases for this purpose, the present inventors have provided a suitable preliminary test, which can easily be carried out by the skilled person in order to initially assess the performance of the subtilase in question.

Thus, the test "Model Detergent Wash Performance Test" disclosed in Example 2, herein, may be employed to assess the efficiency of the selected subtilase. In other words, the "Model Detergent Wash Performance Test" may be employed to assess the ability of a subtilase, when incorporated in a standard detergent composition, to remove egg stains from a standard textile as compared to a reference system, in this case Savinase® (incorporated in the same model detergent system and tested under identical conditions). Using this test, the suitability of a selected subtilase to remove egg stains can be initially investigated, the rationale being that if a selected subtilase does not show a significant improvement in the test compared to Savinase®, it is normally not necessary to carry out further test experiments.

Therefore, subtilases which are particular interesting for the purposes described herein, are such subtilases which, when tested in a model detergent composition comprising

| | |
|---|---|
| 6.2% | LAS (Nansa 80S) |
| 2% | Sodium salt of $C_{16}$–$C_{18}$ fatty acid |
| 4% | Non-ionic surfactant (Plurafax LF404) |
| 22% | Zeolite P |
| 10.5% | $Na_2CO_3$ |
| 4% | $Na_2Si_2O_5$ |
| 2% | Carboxymethylcellulose (CMC) |
| 6.8% | Acrylate liquid CP5 40% |
| 20% | Sodium perborate (empirical formula $NaBO_2.H_2O_2$) |
| 0.2% | EDTA |
| 21% | $Na_2SO_4$ |
| | Water (balance) | as described in the "Model Detergent Wash Performance Test" herein, shows an improved wash performance on egg stains as compared to Savinase® tested under identical conditions.

The improvement in the wash performance may be quantified by employing the so-called "Performance Factor" defined in Example 2, herein.

In a very interesting embodiment of the invention, the subtilase of the invention, when tested in the "Wash Performance Test" has a Performance Factor of at least 1, such as at least 1.5, e.g. at least 2, preferably at least 2.5, such as at least 3, e.g. at least 3.5, in particular at least 4, such as at least 4.5, e.g. at least 5.

Evidently, it is preferred that the subtilase of the invention fulfills the above criteria on at least the stated lowest level, more preferably at the stated intermediate level and most preferably on the stated highest level.

The subtilase of the invention may be constructed by standard techniques for artificial creation of diversity, such as by DNA shuffling of different subtilase genes (see WO 95/22625 and J. E. Ness et al., Nature Biotechnology, 17, 893–896 (1999)).

Obviously, the subtilase of the invention may also be isolated from a natural source, i.e. the subtilase of the invention may, for example, be a bacterial subtilase, e.g. a gram positive bacterial subtilase such as a Bacillus polypeptide, e.g., a Bacillus alkalophilus, Bacillus amyloliquefaciens, Bacillus brevis, Bacillus circulans, Bacillus coagulans, Bacillus lautus, Bacillus lentus, Bacillus licheniformis, Bacillus megaterium, Bacillus stearothermophilus, Bacillus subtilis, or Bacillus thuringiensis subtilase; or a Streptomyces subtilase, e.g., a Streptomyces lividans or Streptomyces murinus subtilase; or a gram negative bacterial subtilase, e.g., an E. coli or a Pseudomonas sp. subtilase.

The subtilase of the present invention may also be a fungal polypeptide, and more preferably a yeast subtilase such as a Candida, Kluyveromyces, Pichia, Saccharomyces, Schizosaccharomyces, or Yarrowia subtilase; or more preferably a filamentous fungal subtilase such as an Acremonium, Aspergillus, Aureobasidium, Cryptococcus, Filibasidium, Fusarium, Humicola, Magnaporthe, Mucor, Myceliophthora, Neocallimastix, Neurospora, Paecilomyces, Penicillium, Piromyces, Schizophyllum, Talaromyces, Thermoascus, Thielavia, Tolypocladium, or Trichoderma subtilase.

In an interesting embodiment, the subtilase is a Saccharomyces carlsbergensis, Saccharomyces cerevisiae, Saccharomyces diastaticus, Saccharomyces douglasii, Saccharomyces kluyveri, Saccharomyces norbensis or Saccharomyces oviformis subtilase.

In another interesting embodiment, the subtilase is an Aspergillus aculeatus, Aspergillus awamori, Aspergillus foetidus, Aspergillus japonicus, Aspergillus nidulans, Aspergillus niger, Aspergillus oryzae, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Trichoderma harzianum, Trichoderma koningii, Trichoderma longibrachiatum, Trichoderma reesei, or Trichoderma viride subtilase.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen und Zellkulturen GmbH (DSM), Centraalbureau Voor Schimmel-cultures (CBS), and Agricultural Research Service Patent Culture Collection, Northern Regional Research Center (NRRL).

Furthermore, such subtilases may be identified and obtained from other sources including microorganisms isolated from nature (e.g., soil, composts, water, etc.) using the above-mentioned probes. Techniques for isolating microorganisms from natural habitats are well known in the art. The nucleic acid sequence may then be derived by similarly screening a genomic or cDNA library of another microorganism. Once a nucleic acid sequence encoding a subtilase has been detected with the probe(s), the sequence may be isolated or cloned by utilizing techniques which are known to those of ordinary skill in the art (see, e.g., Sambrook et al., 1989, supra).

Many methods for cloning a subtilase of the invention and for introducing insertions into genes (e.g. subtilase genes) are well known in the art, cf. the references cited in the "BACK-GROUND OF THE INVENTION" section.

In general standard procedures for cloning of genes and introducing insertions (random and/or site directed) into said genes may be used in order to obtain a subtilase enzyme of the invention. For further description of suitable techniques reference is made to Examples herein (vide infra) and (Sambrook et al. (1989) Molecular cloning: A laboratory manual, Cold Spring Harbor lab., Cold Spring Harbor, N.Y.; Ausubel, F. M. et al. (eds.) "Current protocols in Molecular Biology". John Wiley and Sons, 1995; Harwood, C. R., and Cutting, S. M. (eds.) "Molecular Biological Methods for Bacillus". John Wiley and Sons, 1990); and WO 96/34946.

Further, a subtilase enzyme of the invention may be constructed by standard techniques for artificial creation of diversity, such as by DNA shuffling of different subtilase genes (WO 95/22625; Stemmer WPC, Nature 370:389–91 (1994)). DNA shuffling of e.g. the gene encoding Savinase® with one or more partial subtilase sequences identified in nature will, after subsequent screening for improved wash performance, provide subtilases according to the invention.

NUCLEIC ACID SEQUENCES

The present invention also relates to an isolated nucleic acid sequence, which encodes a subtilase of the present invention.

In one interesting embodiment, the nucleic acid sequence has at least 88% identity with the nucleic acid sequence shown as nucleotides 1 to 807 of SEQ ID NO:1. Preferably, the nucleic acid sequence has at least 89%, at least 90%, at least 91%, at least 92%, at least 93%, at least 94%, at least 95%, at least 96%, at least 97%, at least 98% or at least 99% identity with the nucleic acid sequence shown as nucleotides 1 to 807 of SEQ ID NO:1. In another interesting embodiment of the invention the nucleic acid sequence comprises the nucleic acid sequence shown as nucleotides 1 to 807 of SEQ ID NO:1, an allelic variant thereof, or a fragment thereof capable of encoding a subtilase according to the invention. Obviously, the nucleic acid sequence may consist of the nucleic acid sequence shown as nucleotides 1 to 807 of SEQ ID NO:1.

The present invention also encompasses nucleic acid sequences which encode a polypeptide having the amino acid sequence of SEQ ID NO:2, which differ from SEQ ID NO:1 by virtue of the degeneracy of the genetic code. The present invention also relates to subsequences of SEQ ID NO:1 which encode fragments of SEQ ID NO:2 that have proteolytic activity.

A subsequence of SEQ ID NO:1 is a nucleic acid sequence encompassed by nucleotides 1 to 807 SEQ ID NO:1 except that one or more nucleotides from the 5' and/or 3' end have been deleted.

The present invention also relates to isolated nucleic acid sequences encoding a subtilase of the present invention, which hybridize under low stringency conditions, preferably under medium stringency conditions, more preferably under high stringency conditions, with (i) a complementary strand of the nucleic acid sequence shown as nucleotides 1 to 807 of SEQ ID NO:1, or (ii) a subsequence of (i) of at least 100 nucleotides. The present invention also relates to complementary strands of (i) and (ii).

The techniques used to isolate or clone a nucleic acid sequence encoding a polypeptide are known in the art and include isolation from genomic DNA, preparation from cDNA, or a combination thereof. The cloning of the nucleic acid sequences of the present invention from such genomic DNA can be effected, e.g., by using the well known polymerase chain reaction (PCR) or antibody screening of expression libraries to detect cloned DNA fragments with shared structural features. See, e.g., Innis et al., 1990, PCR: A Guide to Methods and Application, Academic Press, New York. Other nucleic acid amplification procedures such as ligase chain reaction (LCR), ligated activated transcription (LAT) and nucleic acid sequence-based amplification (NASBA) may be used.

An isolated nucleic acid sequence can, for example, be obtained by standard cloning procedures used in genetic engineering to relocate the nucleic acid sequence from its natural location to a different site where it will be reproduced. The cloning procedures may involve excision and isolation of a desired nucleic acid fragment comprising the nucleic acid sequence encoding the subtilase, insertion of the fragment into a vector molecule, and incorporation of the recombinant vector into a host cell where multiple copies or clones of the nucleic acid sequence will be replicated. The nucleic acid sequence may be of genomic, cDNA, RNA, semisynthetic, synthetic origin, or any combinations thereof.

For purposes of the present invention, the degree of identity between two nucleic acid sequences is determined is described above.

Modification of a nucleic acid sequence encoding a subtilase of the present invention may be necessary for the synthesis of subtilases substantially similar to the subtilase. The term "substantially similar" to the subtilase refers to nonnaturally occurring forms of the subtilase. These subtilases may differ in some engineered way from the subtilase isolated from its native source, e.g., variants that differ in specific activity, thermostability, pH optimum, or the like. The variant sequence may be constructed on the basis of the nucleic acid sequence presented as the polypeptide encoding part of SEQ ID NO:1, e.g., a subsequence thereof, and/or by introduction of nucleotide substitutions which do not give rise to another amino acid sequence of the subtilase encoded by the nucleic acid sequence, but which correspond to the codon usage of the host organism intended for production of the enzyme, or by introduction of nucleotide substitutions which may give rise to a different amino acid sequence. For a general description of nucleotide substitution, see, e.g., Ford et al., 1991, Protein Expression and Purification 2: 95–107.

It will be apparent to those skilled in the art that such substitutions can be made outside the regions critical to the function of the molecule and still result in an active subtilase. Amino acid residues essential to the activity of the polypeptide encoded by the isolated nucleic acid sequence of the invention, and therefore preferably not subject to substitution, may be identified according to procedures known in the art, such as site-directed mutagenesis or alanine-scanning mutagenesis (see, e.g., Cunningham and Wells, 1989, Science 244: 1081–1085). In the latter technique, mutations are introduced at every positively charged residue in the molecule, and the resultant mutant molecules are tested for proteolytic activity to identify amino acid residues that are critical to the activity of the molecule. Sites of substrate-enzyme interaction can also be determined by analysis of the three-dimensional structure as determined by such techniques as nuclear magnetic resonance analysis, crystallography or photoaffinity labelling (see, e.g., de Vos et al., 1992, *Science* 255: 306–312; Smith et al., 1992, *Journal of Molecular Biology* 224: 899–904; Wlodaver et al., 1992, *FEBS Letters* 309: 59–64).

NUCLEIC ACID CONSTRUCTS

The present invention also relates to nucleic acid constructs comprising a nucleic acid sequence of the present invention operably linked to one or more control sequences capable of directing the expression of the polypeptide in a suitable host cell.

An isolated nucleic acid sequence encoding a subtilase of the present invention may be manipulated in a variety of ways to provide for expression of the subtilase. Manipulation of the nucleic acid sequence prior to its insertion into a vector may be desirable or necessary depending on the expression vector. The techniques for modifying nucleic acid sequences utilizing recombinant DNA methods are well known in the art.

The control sequences include all components which are necessary or advantageous for the expression of a subtilase of the present invention. Each control sequence may be native or foreign to the nucleic acid sequence encoding the subtilase. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleic acid sequence encoding a subtilase.

The control sequence may be an appropriate promoter sequence, a nucleic acid sequence which is recognized by a host cell for expression of the nucleic acid sequence. The promoter sequence contains transcriptional control sequences which mediate the expression of the subtilase. The promoter may be any nucleic acid sequence which shows transcriptional activity in the host cell of choice including mutant, truncated, and hybrid promoters, and may be obtained from genes encoding extracellular or intracellular subtilases either homologous or heterologous to the host cell.

Examples of suitable promoters for directing the transcription of the nucleic acid constructs of the present invention, especially in a bacterial host cell, are the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (Villa-Kamaroff et al., 1978, *Proceedings of the National Academy of Sciences USA* 75: 3727–3731), as well as the tac promoter (DeBoer et al., 1983, *Proceedings of the National Academy of Sciences USA* 80: 21–25). Further promoters are described in "Useful proteins from recombinant bacteria" in *Scientific American*, 1980, 242: 74–94; and in Sambrook et al., 1989, supra.

Examples of suitable promoters for directing the transcription of the nucleic acid constructs of the present invention in a filamentous fungal host cell are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, and *Fusarium oxysporum* trypsin-like protease (WO 96/00787), as well as the NA2-tpi promoter (a hybrid of the promoters from the genes for *Aspergillus niger* neutral alphaamylase and *Aspergillus oryzae* triose phosphate isomerase), and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH2/GAP), and *Saccharomyces cerevisiae* 3-phosphoglycerate kinase. Other useful promoters for yeast host cells are described by Romanos et al., 1992, *Yeast* 8: 423–488.

The control sequence may also be a suitable transcription terminator sequence, a sequence recognized by a host cell to terminate transcription. The terminator sequence is operably linked to the 3' terminus of the nucleic acid sequence encoding the subtilase. Any terminator which is functional in the host cell of choice may be used in the present invention.

Preferred terminators for filamentous fungal host cells are obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA which is important for translation by the host cell. The leader sequence is operably linked to the 5' terminus of the nucleic acid sequence encoding the polypeptide. Any leader sequence that is functional in the host cell of choice may be used in the present invention.

Preferred leaders for filamentous fungal host cells are obtained from the genes for *Aspergillus oryzae* TAKA amylase and *Aspergillus nidulans* triose phosphate isomerase. Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP). The control sequence may also be a polyadenylation sequence, a sequence operably linked to the 3' terminus of the nucleic acid sequence and which, when transcribed, is recognized by the host cell as a signal to add polyadenosine residues to transcribed mRNA. Any polyadenylation sequence which is functional in the host cell of choice may be used in the present invention.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium* oxysporum trypsin-like protease, and *Aspergillus niger* alpha-glucosidase.

Useful polyadenylation sequences for yeast host cells are described by Guo and Sherman, 1995, *Molecular Cellular Biology* 15: 5983–5990.

The control sequence may also be a signal peptide coding region that codes for an amino acid sequence linked to the amino terminus of a subtilase and directs the encoded subtilase into the cell's secretory pathway. The 5' end of the coding sequence of the nucleic acid sequence may inherently contain a signal peptide coding region naturally linked in translation reading frame with the segment of the coding region which encodes the secreted subtilase. Alternatively, the 5' end of the coding sequence may contain a signal peptide coding region which is foreign to the coding sequence. The foreign signal peptide coding region may be required where the coding sequence does not naturally contain a signal peptide coding region. Alternatively, the foreign signal peptide coding region may simply replace the natural signal peptide coding region in order to enhance secretion of the subtilase. However, any signal peptide coding region which directs the expressed subtilase into the secretory pathway of a host cell of choice may be used in the present invention.

Effective signal peptide coding regions for bacterial host cells are the signal peptide coding regions obtained from the genes for Bacillus NCIB 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109–137.

Effective signal peptide coding regions for filamentous fungal host cells are the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, and *Humicola lanuginosa* lipase.

Useful signal peptides for yeast host cells are obtained from the genes for *Saccharomyces cerevisiae* alpha-factor and *Saccharomyces cerevisiae* invertase. Other useful signal peptide coding regions are described by Romanos et al., 1992, supra.

The control sequence may also be a propeptide coding region that codes for an amino acid sequence positioned at the amino terminus of a subtilase. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* laccase (WO 95/33836).

Where both signal peptide and propeptide regions are present at the amino terminus of a subtilase, the propeptide region is positioned next to the amino terminus of a subtilase and the signal peptide region is positioned next to the amino terminus of the propeptide region.

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the TAKA alpha-amylase promoter, *Aspergillus niger* glucoamylase promoter, and *Aspergillus oryzae* glucoamylase promoter may be used as regulatory sequences. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the nucleic acid sequence encoding the polypeptide would be operably linked with the regulatory sequence.

EXPRESSION VECTORS

The present invention also relates to a recombinant expression vector comprising the nucleic acid construct of the invention, a promoter, and transcriptional and translational stop signals.

The recombinant expression vector comprising the nucleic acid construct encoding the enzyme of the invention may be any vector which may conveniently be subjected to recombinant DNA procedures.

The choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid. Alternatively, the vector may be one that on introduction into a host cell is integrated into the host cell genome in part or in its entirety and replicated together with the chromosome(s) into which it has been integrated.

The vector is preferably an expression vector in which the DNA sequence encoding the enzyme of the invention is operably linked to additional segments required for transcription of the DNA. In general, the expression vector is derived from plasmid or viral DNA, or may contain elements of both. The term, "operably linked" indicates that the segments are arranged so that they function in concert for their intended purposes, e.g. transcription initiates in a promoter and proceeds through the DNA sequence coding for the enzyme.

The promoter may be any DNA sequence which shows transcriptional activity in the host cell of choice and may be derived from genes encoding proteins either homologous or heterologous to the host cell.

Examples of suitable promoters for use in bacterial host cells include the promoter of the *Bacillus stearothermophilus* maltogenic amylase gene, the *Bacillus licheniformis* alphaamylase gene, the *Bacillus amyloliquefaciens* alpha-amylase gene, the *Bacillus subtilis* alkaline protease gen, or the *Bacillus pumilus* xylosidase gene, or the phage Lambda $P_R$ or $P_L$ promoters or the *E. coli* lac, trp or tac promoters.

The DNA sequence encoding the enzyme of the invention may also, if necessary, be operably connected to a suitable terminator.

The recombinant vector of the invention may further comprise a DNA sequence enabling the vector to replicate in the host cell in question.

The vector may also comprise a selectable marker, e.g. a gene the product of which complements a defect in the host cell, or a gene encoding resistance to e.g. antibiotics like kanamycin, chloramphenicol, erythromycin, tetracycline, spectinomycine, or the like, or resistance to heavy metals or herbicides.

To direct an enzyme of the present invention into the secretory pathway of the host cells, a secretory signal sequence (also known as a leader sequence, prepro sequence or pre sequence) may be provided in the recombinant vector. The secretory signal sequence is joined to the DNA sequence encoding the enzyme in the correct reading frame. Secretory signal sequences are commonly positioned 5' to the DNA sequence encoding the enzyme. The secretory signal sequence may be that normally associated with the enzyme or may be from a gene encoding another secreted protein.

The procedures used to ligate the DNA sequences coding for the present enzyme, the promoter and optionally the terminator and/or secretory signal sequence, respectively, or to assemble these sequences by suitable PCR amplification schemes, and to insert them into suitable vectors containing the information necessary for replication or integration, are well known to persons skilled in the art (cf., for instance, Sambrook et al., op.cit.).

HOST CELL

The present invention also relates to a recombinant host cell comprising the nucleic acid construct of the invention.

The DNA sequence encoding the present enzyme introduced into the host cell may be either homologous or heterologous to the host in question. If homologous to the host cell, i.e. produced by the host cell in nature, it will typically be operably connected to another promoter sequence or, if applicable, another secretory signal sequence and/or terminator sequence than in its natural environment. The term "homologous" is intended to include a DNA sequence encoding an enzyme native to the host organism in question. The term "heterologous" is intended to include a DNA sequence not expressed by the host cell in nature. Thus, the DNA sequence may be from another organism, or it may be a synthetic sequence.

The host cell into which the DNA construct or the recombinant vector of the invention is introduced may be any cell which is capable of producing the present enzyme and includes bacteria, yeast, fungi and higher eukaryotic cells including plants.

Examples of bacterial host cells which, on cultivation, are capable of producing the enzyme of the invention are gram-positive bacteria such as strains of Bacillus, such as strains of *B. subtilis, B. licheniformis, B. lentus, B. brevis, B. stearothermophilus, B. alkalophilus, B. amyloliquefaciens, B. coagulans, B. circulans, B. lautus, B. megatherium* or *B. thuringiensis*, in particular *B. lentus*, or strains of Streptomyces, such as *S. lividans* or *S. murinus*, or gram-negative bacteria such as *Echerichia coli*.

The transformation of the bacteria may be effected by protoplast transformation, electroporation, conjugation, or by using competent cells in a manner known per se (cf. Sambrook et al., supra).

When expressing the enzyme in bacteria such as *E. coli*, the enzyme may be retained in the cytoplasm, typically as insoluble granules (known as inclusion bodies), or may be directed to the periplasmic space by a bacterial secretion sequence. In the former case, the cells are lysed and the granules are recovered and denatured after which the enzyme is refolded by diluting the denaturing agent. In the latter case, the enzyme may be recovered from the periplasmic space by disrupting the cells, e.g. by sonication or osmotic shock, to release the contents of the periplasmic space and recovering the enzyme.

When expressing the enzyme in gram-positive bacteria such as Bacillus or Streptomyces strains, the enzyme may be retained in the cytoplasm, or may be directed to the extracellular medium by a bacterial secretion sequence. In the latter case, the enzyme may be recovered from the medium as described below.

In another embodiment of the invention, the fungal host cell is a yeast cell. "Yeast" as used herein includes ascosporogenous yeast (Endomycetales), basidiosporogenous yeast, and yeast be-longing to the Fungi Imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, *Soc. App. Bacteriol. Symposium Series* No. 9, 1980).

In a preferred embodiment, the yeast host cell is a Candida, Hansenula, Kluyveromyces, Pichia, Saccharomyces, Schizosaccharomyces, or Yarrowia cell.

In a most preferred embodiment, the yeast host cell is a *Saccharomyces carlsbergensis, Saccharomyces cerevisiae, Saccharomyces diastaticus, Saccharomyces douglasii, Saccharomyces kluyveri, Saccharomyces norbensis* or *Saccharomyces oviformis* cell. In another most preferred embodiment, the yeast host cell is a *Kluyveromyces lactis* cell. In another most preferred embodiment, the yeast host cell is a *Yarrowia lipolytica* cell.

In another preferred embodiment, the fungal host cell is a filamentous fungal cell. "Filamentous fungi" include all filamentous forms of the subdivision Eumycota and Oomycota (as defined by Hawksworth et al., 1995, supra). The filamentous fungi are characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In an even more preferred embodiment, the filamentous fungal host cell is a cell of a species of, but not limited to, Acremonium, Aspergillus, Fusarium, Humicola, Mucor, Myceliophthora, Neurospora, Penicillium, Thielavia, Tolypocladium, or Trichoderma.

In a most preferred embodiment, the filamentous fungal host cell is an *Aspergillus awamori, Aspergillus foetidus, Aspergillus japonicus, Aspergillus nidulans, Aspergillus niger* or *Aspergillus oryzae* cell. In another most preferred embodiment, the filamentous fungal host cell is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides*, or *Fusarium venenatum* cell. In an even most preferred embodiment, the filamentous fungal parent cell is a *Fusarium venenatum* (Nirenberg sp. nov.) cell. In another most preferred embodiment, the filamentous fungal host cell is a *Humicola insolens, Humicola lanuginosa, Mucor miehei, Myceliophthora thermophila, Neurospora crassa, Penicillium purpurogenum, Thielavia terrestris, Trichoderma harzianum, Trichoderma koningii, Trichoderma longibrachiatum, Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of Aspergillus host cells are described in EP 238 023 and Yelton et al., 1984, *Proceedings of the National Academy of Sciences USA* 81: 1470–1474. Suitable methods for transforming Fusarium species are described by Malardier et al., 1989, *Gene* 78: 147–156 and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182–187, Academic Press, Inc., New York; Ito et al., 1983, *Journal of Bacteriology* 153: 163; and Hinnen et al., 1978, *Proceedings of the National Academy of Sciences USA* 75: 1920.

METHOD OF PRODUCING A SUBTILASES OF THE INVENTION

The present invention further relates to a method for producing a subtilase of the invention, the method comprising:

a) cultivating a recombinant host cell of the invention under conditions conducive to the production of the subtilase; and b) recovering the subtilase.

When an expression vector comprising a DNA sequence encoding the enzyme is transformed into a heterologous host cell it is possible to enable heterologous recombinant production of the enzyme of the invention.

Thereby it is possible to make a highly purified subtilase composition, characterized in being free from homologous impurities.

In this context homologous impurities means any impurities (e.g. other polypeptides than the enzyme of the invention) which originate from the homologous cell where the enzyme of the invention is originally obtained from.

The medium used to culture the transformed host cells may be any conventional medium suitable for growing the host cells in question. The expressed subtilase may conveniently be secreted into the culture medium and may be recovered therefrom by well-known procedures including separating the cells from the medium by centrifugation or filtration, precipitating proteinaceous components of the medium by means of a salt such as ammonium sulfate, followed by chromatographic procedures such as ion exchange chromatography, affinity chromatography, or the like.

USE OF A SUBTILASE OF THE INVENTION

A subtilase enzyme of the invention may be used for a number of industrial applications, in particular within the detergent industry. Thus, the present invention also relates to a cleaning or detergent composition, preferably a laundry or dishwash composition, comprising the subtilase enzyme of the invention.

DETERGENT COMPOSITIONS COMPRISING THE SUBTILASE ENZYME OF THE INVENTION

In general, cleaning and detergent compositions are well described in the art and reference is made to WO 96/34946; WO 97/07202; WO 95/30011 for further description of suitable cleaning and detergent compositions.

Furthermore the examples herein demonstrate the improvements in wash performance on egg stains for the subtilases of the invention.

Detergent Compositions

The enzyme of the invention may be added to and thus become a component of a cleaning or detergent composition.

The detergent composition of the invention may for example be formulated as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dishwashing operations.

In a specific aspect, the invention provides a detergent additive comprising the subtilase enzyme of the invention. The detergent additive as well as the detergent composition may comprise one or more other enzymes such as another protease, a lipase, a cutinase, an amylase, a carbohydrase, a cellulase, a pectinase, a mannanase, an arabinase, a galactanase, a xylanase, an oxidase, e.g., a laccase, and/or a peroxidase.

In general the properties of the chosen enzyme(s) should be compatible with the selected detergent, (i.e. pH-optimum, compatibility with other enzymatic and non-enzymatic ingredients, etc.), and the enzyme(s) should be present in effective amounts.

Proteases: Suitable proteases include those of animal, vegetable or microbial origin. Microbial origin is preferred. Chemically modified or protein engineered mutants are included. The protease may be a serine protease or a metallo protease, preferably an alkaline microbial protease or a trypsin-like protease. Examples of alkaline proteases are subtilisins, especially those derived from Bacillus, e.g., subtilisin Novo, subtilisin Carlsberg, subtilisin 309, subtilisin 147 and subtilisin 168 (described in WO 89/06279). Examples of trypsin-like proteases are trypsin (e.g. of porcine or bovine origin) and the Fusarium protease described in WO 89/06270 and WO 94/25583.

Examples of useful proteases are the variants described in WO 92/19729, WO 98/20115, WO 98/20116, and WO 98/34946, especially the variants with substitutions in one or more of the following positions: 27, 36, 57, 76, 87, 97, 101, 104, 120, 123, 167, 170, 194, 206, 218, 222, 224, 235 and 274.

Preferred commercially available protease enzymes include Alcalase™, Savinase™, Primase™, Duralase™, Esperase™, and Kannase™ (Novo Nordisk A/S), Maxatase™, Maxacal™, Maxapem™, Properase™, Purafect™, Purafect OxP™, FN2™, and FN3™ (Genencor International Inc.).

Lipases: Suitable lipases include those of bacterial or fungal origin. Chemically modified or protein engineered mutants are included. Examples of useful lipases include lipases from Humicola (synonym Thermomyces), e.g. from *H. lanuginosa* (*T. lanuginosus*) as described in EP 258 068 and EP 305 216 or from *H. insolens* as described in WO 96/13580, a Pseudomonas lipase, e.g. from *P. alcaligenes* or *P. pseudoalcaligenes* (EP 218 272), *P. cepacia* (EP 331 376), *P. stutzeri* (GB 1,372,034), *P. fluorescens*, Pseudomonas sp. strain SD 705 (WO 95/06720 and WO 96/27002), *P. wisconsinensis* (WO 96/12012), a Bacillus lipase, e.g. from *B. subtilis* (Dartois et al. (1993), Biochemica et Biophysica Acta, 1131, 253–360), *B. stearothermophilus* (JP 64/744992) or *B. pumilus* (WO 91/16422). ™Other examples are lipase variants such as those described in WO 92/05249, WO 94/01541, EP 407 225, EP 260 105, WO 95/35381, WO 96/00292, WO 95/30744, WO 94/25578, WO 95/14783, WO 95/22615, WO 97/04079 and WO 97/07202.

Preferred commercially available lipase enzymes include Lipolase™ and Lipolase Ultra™ (Novo Nordisk A/S).

Amylases: Suitable amylases (α and/or β) include those of bacterial or fungal origin. Chemically modified or protein engineered mutants are included. Amylases include, for example, α-amylases obtained from Bacillus, e.g. a special strain of *B. licheniformis*, described in more detail in GB 1,296,839.

Examples of useful amylases are the variants described in WO 94/02597, WO 94/18314, WO 96/23873, and WO 97/43424, especially the variants with substitutions in one or more of the following positions: 15, 23, 105, 106, 124, 128, 133, 154, 156, 181, 188, 190, 197, 202, 208, 209, 243, 264, 304, 305, 391, 408, and 444.

Commercially available amylases are Duramyl™, Termamyl™, Fungamyl™ and BAN™ (Novo Nordisk A/S), Rapidase™ and Purastar™ (from Genencor International Inc.).

Cellulases: Suitable cellulases include those of bacterial or fungal origin. Chemically modified or protein engineered mutants are included. Suitable cellulases include cellulases from the genera Bacillus, Pseudomonas, Humicola, Fusarium, Thielavia, Acremonium, e.g. the fungal cellulases produced from *Humicola insolens, Myceliophthora thermophila* and *Fusarium oxysporum* disclosed in U.S. Pat. No. 4,435,307, U.S. Pat. No. 5,648,263, U.S. Pat. No. 5,691,178, U.S. Pat. No. 5,776,757 and WO 89/09259.

Especially suitable cellulases are the alkaline or neutral cellulases having colour care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. No. 5,457,046, U.S. Pat. No. 5,686,593, U.S. Pat. No. 5,763,254, WO 95/24471, WO 98/12307 and PCT/DK98/00299.

Commercially available cellulases include Celluzyme™, and Carezyme™ (Novo Nordisk A/S), Clazinase™, and Puradax HA™ (Genencor International Inc.), and KAC-500 (B)™ (Kao Corporation).

Peroxidases/Oxidases: Suitable peroxidases/oxidases include those of plant, bacterial or fungal origin. Chemically modified or protein engineered mutants are included. Examples of useful peroxidases include peroxidases from Coprinus, e.g. from *C. cinereus*, and variants thereof as those described in WO 93/24618, WO 95/10602, and WO 98/15257.

Commercially available peroxidases include Guardzyme™ (Novo Nordisk A/S).

The detergent enzyme(s) may be included in a detergent composition by adding separate additives containing one or more enzymes, or by adding a combined additive comprising all of these enzymes. A detergent additive of the invention, i.e. a separate additive or a combined additive, can be formulated e.g. as a granulate, a liquid, a slurry, etc. Preferred detergent additive formulations are granulates, in particular non-dusting granulates, liquids, in particular stabilized liquids, or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

The detergent composition of the invention may be in any convenient form, e.g., a bar, a tablet, a powder, a granule, a paste or a liquid. A liquid detergent may be aqueous, typically containing up to 70% water and 0–30% organic solvent, or non-aqueous.

The detergent composition typically comprises one or more surfactants, which may be non-ionic including semi-polar and/or anionic and/or cationic and/or zwitterionic. The surfactants are typically present at a level of from 0.1% to 60% by weight. When included therein the detergent will usually contain from about 1% to about 40% of an anionic surfactant such as linear alkylbenzenesulfonate, alpha-olefinsulfonate, alkyl sulfate (fatty alcohol sulfate), alcohol ethoxysulfate, secondary alkanesulfonate, alpha-sulfo fatty acid methyl ester, alkyl- or alkenylsuccinic acid or soap.

When included therein the detergent will usually contain from about 0.2% to about 40% of a non-ionic surfactant such as alcohol ethoxylate, nonylphenol ethoxylate, alkylpolyglycoside, alkyldimethylamineoxide, ethoxylated fatty acid monoethanolamide, fatty acid monoethanolamide, polyhydroxy alkyl fatty acid amide, or N-acyl N-alkyl derivatives of glucosamine ("glucamides").

The detergent may contain 0–65% of a detergent builder or complexing agent such as zeolite, diphosphate, triphosphate, phosphonate, carbonate, citrate, nitrilotriacetic acid, ethyl-enediaminetetraacetic acid, diethylenetriaminepentaacetic acid, alkyl- or alkenylsuccinic acid, soluble silicates or layered silicates (e.g. SKS-6 from Hoechst).

The detergent may comprise one or more polymers. Examples are carboxymethylcellulose, poly (vinylpyrrolidone), poly(ethylene glycol), poly(vinyl alcohol), poly(vinylpyridine-N-oxide), poly (vinylimidazole), polycarboxylates such as polyacrylates, maleic/acrylic acid copolymers and lauryl methacrylate/acrylic acid copolymers.

The detergent may contain a bleaching system which may comprise a $H_2O_2$ source such as perborate or percarbonate which may be combined with a peracid-forming bleach activator such as tetraacetylethylenediamine or nonanoyloxybenzenesulfonate. Alternatively, the bleaching system may comprise peroxyacids of e.g. the amide, imide, or sulfone type.

The enzyme(s) of the detergent composition of the invention may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid, and the composition may be formulated as described in e.g. WO 92/19709 and WO 92/19708.

The detergent may also contain other conventional detergent ingredients such as e.g. fabric conditioners including clays, foam boosters, suds suppressors, anti-corrosion agents, soil-suspending agents, anti-soil redeposition agents, dyes, bactericides, optical brighteners, hydrotropes, tarnish inhibitors, or perfumes.

It is at present contemplated that in the detergent compositions any enzyme, in particular the enzyme of the invention, may be added in an amount corresponding to 0.01–100 mg of enzyme protein per liter of wash liquor, preferably 0.05–5 mg of enzyme protein per liter of wash liquor, in particular 0.1–1 mg of enzyme protein per liter of wash liquor.

The enzyme of the invention may additionally be incorporated in the detergent formulations disclosed in WO 97/07202 which is hereby incorporated as reference.

The invention is described in further detail in the following examples which, are not in any way intended to limit the scope of the invention as claimed.

In the detergent compositions, the abbreviated component identifications have the following meanings:

LAS: Sodium linear $C_{12}$ alkyl benzene sulphonate

TAS: Sodium tallow alkyl sulphate

XYAS: Sodium $C_{1X}$–$C_{1Y}$ alkyl sulfate

SS: Secondary soap surfactant of formula 2-butyl octanoic acid

25EY: A $C_{12}$–$C_{15}$ predominantly linear primary alcohol condensed with an average of Y moles of ethylene oxide 45EY: A $C_{14}$–$C_{15}$ predominantly linear primary alcohol condensed with an average of Y moles of ethylene oxide XYEZS: $C_X$–$C_Y$ sodium alkyl sulfate condensed with an average of Z moles of ethylene oxide per mole Nonionic: $C_{13}$–$C_{15}$ mixed ethoxylated/propoxylated fatty alcohol with an average degree of ethoxylation of 3.8 and an average degree of propoxylation of 4.5 sold under the tradename Plurafax LF404 by BASF GmbH CFAA: $C_{12}$–$C_{14}$ alkyl N-methyl glucamide TFAA: $C_{16}$–$C_{18}$ alkyl N-methyl glucamide Silicate: Amorphous Sodium Silicate ($SiO_2$:$Na_2O$ ratio=2.0)

NaSKS-6: Crystalline layered silicate of formula δ-$Na_2Si_2O_5$

Carbonate: Anhydrous sodium carbonate

Phosphate: Sodium tripolyphosphate

MA/AA: Copolymer of 1:4 maleic/acrylic acid, average molecular weight about 80,000

Polyacrylate: Polyacrylate homopolymer with an average molecular weight of 8,000 sold under the tradename PA30 by BASF Gmbh Zeolite A: Hydrated Sodium Aluminosilicate of formula $Na_{12}(AlO_2SiO_2)_{12} \cdot 27H_2O$ having a primary particle size in the range from 1 to 10 micrometers Citrate: Tri-sodium citrate dihydrate Citric: Citric Acid Perborate: Anhydrous sodium perborate monohydrate bleach, empirical formula $NaBO_2 \cdot H_2O_2$ PB4: Anhydrous sodium perborate tetrahydrate Percarbonate: Anhydrous sodium percarbonate bleach of empirical formula $2Na_2CO_3 \cdot 3H_2O_2$ TAED: Tetraacetyl ethylene diamine CMC: Sodium carboxymethyl cellulose DETPMP: Diethylene triamine penta (methylene phosphonic acid), marketed by Monsanto under the Tradename Dequest 2060

PVP: Polyvinylpyrrolidone polymer

EDDS: Ethylenediamine-N,N'-disuccinic acid, [S,S] isomer in the form of the sodium salt Suds 25% paraffin wax Mpt 50° C., 17% hydrophobic silica, Suppressor: 58% paraffin oil Granular Suds 12% Silicone/silica, 18% stearyl alcohol, 70% suppressor: starch in granular form

Sulphate: Anhydrous sodium sulphate

HMWPEO: High molecular weight polyethylene oxide

TAE 25: Tallow alcohol ethoxylate (25)

Detergent Example I

A granular fabric cleaning composition in accordance with the invention may be prepared as follows:

| | |
|---|---|
| Sodium linear $C_{12}$ alkyl benzene sulfonate | 6.5 |
| Sodium sulfate | 15.0 |
| Zeolite A | 26.0 |
| Sodium nitrilotriacetate | 5.0 |
| Enzyme | 0.1 |
| PVP | 0.5 |
| TAED | 3.0 |
| Boric acid | 4.0 |
| Perborate | 18.0 |
| Phenol sulphonate | 0.1 |
| Minors | up to 100% |

Detergent Example II

A compact granular fabric cleaning composition (density 800 g/l) in accord with the invention may be prepared as follows:

| | |
|---|---|
| 45AS | 8.0 |
| 25E3S | 2.0 |
| 25E5 | 3.0 |
| 25E3 | 3.0 |
| TFAA | 2.5 |
| Zeolite A | 17.0 |
| NaSKS-6 | 12.0 |
| Citric acid | 3.0 |
| Carbonate | 7.0 |
| MA/AA | 5.0 |
| CMC | 0.4 |
| Enzyme | 0.1 |
| TAED | 6.0 |
| Percarbonate | 22.0 |
| EDDS | 0.3 |
| Granular suds suppressor | 3.5 |
| water/minors | Up to 100% |

Detergent Example III

Granular fabric cleaning compositions in accordance with the invention which are especially useful in the laundering of coloured fabrics were prepared as follows:

| | | |
|---|---|---|
| LAS | 10.7 | — |
| TAS | 2.4 | — |
| TFAA | — | 4.0 |
| 45AS | 3.1 | 10.0 |
| 45E7 | 4.0 | — |
| 25E3S | — | 3.0 |
| 68E11 | 1.8 | — |

| | | |
|---|---|---|
| -continued | | |
| 25E5 | — | 8.0 |
| Citrate | 15.0 | 7.0 |
| Carbonate | — | 10.0 |
| Citric acid | 2.5 | 3.0 |
| Zeolite A | 32.1 | 25.0 |
| Na-SKS-6 | — | 9.0 |
| MA/AA | 5.0 | 5.0 |
| DETPMP | 0.2 | 0.8 |
| Enzyme | 0.10 | 0.05 |
| Silicate | 2.5 | — |
| Sulphate | 5.2 | 3.0 |
| PVP | 0.5 | — |
| Poly (4-vinylpyridine)-N-Oxide/copolymer of vinyl-imidazole and vinyl-pyrrolidone | — | 0.2 |
| Perborate | 1.0 | — |
| Phenol sulfonate | 0.2 | — |
| Water/Minors | Up to 100% | |

Detergent Example IV

Granular fabric cleaning compositions in accordance with the invention which provide "Softening through the wash" capability may be prepared as follows:

| | | |
|---|---|---|
| 45AS | — | 10.0 |
| LAS | 7.6 | — |
| 68AS | 1.3 | — |
| 45E7 | 4.0 | — |
| 25E3 | — | 5.0 |
| Coco-alkyl-dimethyl hydroxy-ethyl ammonium chloride | 1.4 | 1.0 |
| Citrate | 5.0 | 3.0 |
| Na-SKS-6 | — | 11.0 |
| Zeolite A | 15.0 | 15.0 |
| MA/AA | 4.0 | 4.0 |
| DETPMP | 0.4 | 0.4 |
| Perborate | 15.0 | — |
| Percarbonate | — | 15.0 |
| TAED | 5.0 | 5.0 |
| Smectite clay | 10.0 | 10.0 |
| HMWPEO | — | 0.1 |
| Enzyme | 0.10 | 0.05 |
| Silicate | 3.0 | 5.0 |
| Carbonate | 10.0 | 10.0 |
| Granular suds suppressor | 1.0 | 4.0 |
| CMC | 0.2 | 0.1 |
| Water/Minors | Up to 100% | |

Detergent Example V

Heavy duty liquid fabric cleaning compositions in accordance with the invention may be prepared as follows:

| | | |
|---|---|---|
| LAS acid form | — | 25.0 |
| Citric acid | 5.0 | 2.0 |
| 25AS acid form | 8.0 | — |
| 25AE2S acid form | 3.0 | — |
| 25AE7 | 8.0 | — |
| CFAA | 5 | — |
| DETPMP | 1.0 | 1.0 |
| Fatty acid | 8 | — |
| Oleic acid | — | 1.0 |
| Ethanol | 4.0 | 6.0 |
| Propanediol | 2.0 | 6.0 |
| Enzyme | 0.10 | 0.05 |

| | | |
|---|---|---|
| -continued | | |
| Coco-alkyl dimethyl hydroxy ethyl ammonium chloride | — | 3.0 |
| Smectite clay | — | 5.0 |
| PVP | 2.0 | — |
| Water/Minors | Up to 100% | |

Powder Automatic Dishwash Composition I

| | |
|---|---|
| Nonionic surfactant | 0.4–2.5% |
| Sodium metasilicate | 0–20% |
| Sodium disilicate | 3–20% |
| Sodium triphosphate | 20–40% |
| Sodium carbonate | 0–20% |
| Sodium perborate | 2–9% |
| Tetraacetyl ethylene diamine (TAED) | 1–4% |
| Sodium sulphate | 5–33% |
| Enzymes | 0.0001–0.1% |

Powder Automatic Dishwash Composition II

| | |
|---|---|
| Nonionic surfactant (e.g. alcohol ethoxylate) | 1–2% |
| Sodium disilicate | 2–30% |
| Sodium carbonate | 10–50% |
| Sodium phosphonate | 0–5% |
| Trisodium citrate dihydrate | 9–30% |
| Nitrilotrisodium acetate (NTA) | 0–20% |
| Sodium perborate monohydrate | 5–10% |
| Tetraacetyl ethylene diamine (TAED) | 1–2% |
| Polyacrylate polymer (e.g. maleic acid/acrylic acid co-polymer) | 6–25% |
| Enzymes | 0.0001–0.1% |
| Perfume | 0.1–0.5% |
| Water | 5–10 |

Powder Automatic Dishwash Composition III

| | |
|---|---|
| Nonionic surfactant | 0.5–2.0% |
| Sodium disilicate | 25–40% |
| Sodium citrate | 30–55% |
| Sodium carbonate | 0–29% |
| Sodium bicarbonate | 0–20% |
| Sodium perborate monohydrate | 0–15% |
| Tetraacetyl ethylene diamine (TAED) | 0–6% |
| Maleic acid/acrylic acid copolymer | 0–5% |
| Clay | 1–3% |
| Polyamino acids | 0–20% |
| Sodium polyacrylate | 0–8% |
| Enzymes | 0.0001–0.1% |

Powder Automatic Dishwash Composition IV

| | |
|---|---|
| Nonionic surfactant | 1–2% |
| Zeolite MAP | 15–42% |
| Sodium disilicate | 30–34% |
| Sodium citrate | 0–12% |
| Sodium carbonate | 0–20% |

-continued

| | |
|---|---|
| Sodium perborate monohydrate | 7–15% |
| Tetraacetyl ethylene diamine (TAED) | 0–3% |
| Polymer | 0–4% |
| Maleic acid/acrylic acid copolymer | 0–5% |
| Organic phosphonate | 0–4% |
| Clay | 1–2% |
| Enzymes | 0.0001–0.1% |
| Sodium sulphate | Balance |

Powder Automatic Dishwash Composition V

| | |
|---|---|
| Nonionic surfactant | 1–7% |
| Sodium disilicate | 18–30% |
| Trisodium citrate | 10–24% |
| Sodium carbonate | 12–20% |
| Monopersulphate (2 $KHSO_5 \cdot KHSO_4 \cdot K_2SO_4$) | 15–21% |
| Bleach stabilizer | 0.1–2% |
| Maleic acid/acrylic acid copolymer | 0–6% |
| Diethylene triamine pentaacetate, pentasodium salt | 0–2.5% |
| Enzymes | 0.0001–0.1% |
| Sodium sulphate, water | Balance |

Powder and Liquid Dishwash Composition With Cleaning Surfactant System VI

| | |
|---|---|
| Nonionic surfactant | 0–1.5% |
| Octadecyl dimethylamine N-oxide dihydrate | 0–5% |
| 80:20 wt.C18/C16 blend of octadecyl dimethylamine N-oxide dihydrate and hexadecyldimethyl amine N-oxide dihydrate | 0–4% |
| 70:30 wt.C18/C16 blend of octadecyl bis (hydroxyethyl)amine N-oxide anhydrous and hexadecyl bis (hydroxyethyl)amine N-oxide anhydrous | 0–5% |
| $C_{13}$–$C_{15}$ alkyl ethoxysulfate with an average degree of ethoxylation of 3 | 0–10% |
| $C_{12}$–$C_{15}$ alkyl ethoxysulfate with an average degree of ethoxylation of 3 | 0–5% |
| $C_{13}$–$C_{15}$ ethoxylated alcohol with an average degree of ethoxylation of 12 | 0–5% |
| A blend of $C_{12}$–$C_{15}$ ethoxylated alcohols with an average degree of ethoxylation of 9 | 0–6.5% |
| A blend of $C_{13}$–$C_{15}$ ethoxylated alcohols with an average degree of ethoxylation of 30 | 0–4% |
| Sodium disilicate | 0–33% |
| Sodium tripolyphosphate | 0–46% |
| Sodium citrate | 0–28% |
| Citric acid | 0–29% |
| Sodium carbonate | 0–20% |
| Sodium perborate monohydrate | 0–11.5% |
| Tetraacetyl ethylene diamine (TAED) | 0–4% |
| Maleic acid/acrylic acid copolymer | 0–7.5% |
| Sodium sulphate | 0–12.5% |
| Enzymes | 0.0001–0.1% |

Non-aqueous Liquid Automatic Dishwashing Composition VII

| | |
|---|---|
| Liquid nonionic surfactant (e.g. alcohol ethoxylates) | 2.0–10.0% |
| Alkali metal silicate | 3.0–15.0% |
| Alkali metal phosphate | 20.0–40.0% |
| Liquid carrier selected from higher glycols, polyglycols, polyoxides, glycolethers | 25.0–45.0% |
| Stabilizer (e.g. a partial ester of phosphoric acid and a $C_{16}$–$C_{18}$ alkanol) | 0.5–7.0% |
| Foam suppressor (e.g. silicone) | 0–1.5% |
| Enzymes | 0.0001–0.1% |

Non-aqueous Liquid Dishwashing Composition VIII

| | |
|---|---|
| Liquid nonionic surfactant (e.g. alcohol ethoxylates) | 2.0–10.0% |
| Sodium silicate | 3.0–15.0% |
| Alkali metal carbonate | 7.0–20.0% |
| Sodium citrate | 0.0–1.5% |
| Stabilizing system (e.g. mixtures of finely divided silicone and low molecular weight dialkyl polyglycol ethers) | 0.5–7.0% |
| Low molecule weight polyacrylate polymer | 5.0–15.0% |
| Clay gel thickener (e.g. bentonite) | 0.0–10.0% |
| Hydroxypropyl cellulose polymer | 0.0–0.6% |
| Enzymes | 0.0001–0.1% |
| Liquid carrier selected from higher lycols, polyglycols, polyoxides and glycol ethers | Balance |

Thixotropic Liquid Automatic Dishwashing Composition IX

| | |
|---|---|
| $C_{12}$–$C_{14}$ fatty acid | 0–0.5% |
| Block co-polymer surfactant | 1.5–15.0% |
| Sodium citrate | 0–12% |
| Sodium tripolyphosphate | 0–15% |
| Sodium carbonate | 0–8% |
| Aluminium tristearate | 0–0.1% |
| Sodium cumene sulphonate | 0–1.7% |
| Polyacrylate thickener | 1.32–2.5% |
| Sodium polyacrylate | 2.4–6.0% |
| Boric acid | 0–4.0% |
| Sodium formate | 0–0.45% |
| Calcium formate | 0–0.2% |
| Sodium n-decydiphenyl oxide disulphonate | 0–4.0% |
| Monoethanol amine (MEA) | 0–1.86% |
| Sodium hydroxide (50%) | 1.9–9.3% |
| 1,2-Propanediol | 0–9.4% |
| Enzymes | 0.0001–0.1% |
| Suds suppressor, dye, perfumes, water | Balance |

Liquid Automatic Dishwashing Composition X

| | |
|---|---|
| Alcohol ethoxylate | 0–20% |
| Fatty acid ester sulphonate | 0–30% |

-continued

| | |
|---|---|
| Sodium dodecyl sulphate | 0–20% |
| Alkyl polyglycoside | 0–21% |
| Oleic acid | 0–10% |
| Sodium disilicate monohydrate | 18–33% |
| Sodium citrate dihydrate | 18–33% |
| Sodium stearate | 0–2.5% |
| Sodium perborate monohydrate | 0–13% |
| Tetraacetyl ethylene diamine (TAED) | 0–8% |
| Maleic acid/acrylic acid copolymer | 4–8% |
| Enzymes | 0.0001–0.1% |

Liquid Automatic Dishwashing Composition
Containing Protected Bleach Particles XI

| | |
|---|---|
| Sodium silicate | 5–10% |
| Tetrapotassium pyrophosphate | 15–25% |
| Sodium triphosphate | 0–2% |
| Potassium carbonate | 4–8% |
| Protected bleach particles, e.g. chlorine | 5–10% |
| Polymeric thickener | 0.7–1.5% |
| Potassium hydroxide | 0–2% |
| Enzymes | 0.0001–0.1% |
| Water | Balance |

XII: Automatic dishwashing compositions as described in I, II, III, IV, VI and X, wherein perborate is replaced by percarbonate.

XIII: Automatic dishwashing compositions as described in I–VI, which additionally contain a manganese catalyst. The manganese catalyst may, e.g., be one of the compounds described in "Efficient manganese catalysts for low-temperature bleaching", Nature, (1994), 369, 637–639.

MATERIALS AND METHODS

PROTEOLYTIC ACTIVITY

In the context of this invention proteolytic activity is expressed in Kilo NOVO Protease Units (KNPU). The activity is determined relatively to an enzyme standard (SAVINASE ), and the determination is based on the digestion of a dimethyl casein (DMC) solution by the proteolytic enzyme at standard conditions, i.e. 50° C., pH 8.3, 9 min. reaction time, 3 min. measuring time. A folder AF 220/1 is available upon request to Novo Nordisk A/S, Denmark, which folder is hereby included by reference.

A GU is a Glycine Unit, defined as the proteolytic enzyme activity which, under standard conditions, during a 15 minutes' incubation at 40° C., with N-acetyl casein as substrate, produces an amount of $NH_2$-group equivalent to 1 mmole of glycine.

Enzyme activity can also be measured using the PNA assay, according to reaction with the soluble substrate succinylalanine-alanine-proline-phenyl-alanine-para-nitrophenol, which is described in the Journal of American Oil Chemists Society, Rothgeb, T. M., Goodlander, B. D., Garrison, P. H., and Smith, L. A., (1988).

EXAMPLE 1

Construction and Expression of Subtilases According to the Invention

The subtilisin having the amino acid sequence shown in SEQ ID NO:2 was located in vector pJRoC112, which is very similar to plasmid pKH400 (previously described in WO 98/41623). The plasmids are identical outside the regions encoding the mature subtilisin, i.e. the origin of replication, the cat gene conferring resistance towards chloramphenicol, the promoter directing the initiation of transcription of the subtilisin and the pre/pro regions from Savinase® are identical in these plasmids. Differences are only found within the part of the gene encoding the mature subtilisin.

This plasmid replicates both in *E. coli* and in *Bacillus subtilis*. In *Bacillus subtilis* the subtilisin according to the invention was expressed from this plasmid. Fermentation and purification of the protease is described below.

PKH400 was constructed from pJS3 (*E. coli*—*B. subtilis* shuttle vector containing a synthetic gene encoding for subtilase 309 (Savinase®) as described by J. Schiødt et al. in *Protein and Peptide Letters*, 3, 39–44 (1996)) by introduction of two BamHI sites at positions 1841 and 3730.

The mature gene has been subcloned into plasmid pzero-2 (Invitrogen, Groningen, The Nederlands). An approximately 1240 bp PmeI-BamHI fragment containing the complete mature region of the subtilase having the amino acid sequence shown in SEQ ID NO:2 was ligated with vector pZero-2 and digested with restriction endonucleases BamHI-EcoRV. The ligation mixture was transformed into competent *E.coli* cells. Transformants, were analysed by PCR to verify the presence of the inserted fragment and the part of this fragment encoding the mature subtilisin was sequenced. The resulting plasmid, denoted pTVB364, was deposited on Feb. 10, 2000 at DSMZ and was given the accession number DSM 13306.

Fermentation

Fermentations for the production of subtilase enzymes were performed at 30° C. on a rotary shaking table (300 r.p.m.) in 500 ml baffled Erlenmeyer flasks containing 100 ml BPX medium for 5 days.

Consequently, in order to make, e.g., a 2 liter broth 20 Erlenmeyer flasks were fermented simultaneously.

Media

| BPX Medium Composition (per liter) | |
|---|---|
| Potato starch | 100 g |
| Ground barley | 50 g |
| Soybean flour | 20 g |
| $Na_2HPO_4 \times 12H_2O$ | 9 g |
| Pluronic | 0.1 g |
| Sodium caseinate | 10 g |

The starch in the medium was liquefied with α-amylase and the medium was sterilized by heating at 120° C. for 45 minutes. After sterilization the pH of the medium was adjusted to 9 by addition of $NaHCO_3$ to 0.1 M.

Purification

This procedure relates to purification of a 2 liter scale fermentation for the production of the subtilases of the invention in a Bacillus host cell.

Approximately 1.6 liters of fermentation broth was centrifuged at 5000 rpm for 35 minutes in 1 liter beakers. The supernatants were adjusted to pH 6.5 using 10% acetic acid and filtered on Seitz Supra S100 filter plates.

The filtrates were concentrated to approximately 400 ml using an Amicon CH2A UF unit equipped with an Amicon S1Y10 UF cartridge. The UF concentrate was centrifuged and filtered at room temperature prior to absorption on a Bacitracin affinity 10 column at pH 7. The subtilase was eluted from the Bacitracin column at room temperature using 25% 2-propanol and 1 M sodium chloride in a buffer solution with 0.01 dimethylglutaric acid, 0.1 M boric acid and 0.002 M calcium chloride adjusted to pH 7.

The fractions with protease activity from the Bacitracin purification step were combined and applied to 750 ml Sephadex G25 column (5 cm diameter) equilibrated with a buffer containing 0.01 M dimethylglutaric acid, 0.2 M boric acid and 0.002 M calcium chloride adjusted to pH 6.5.

Fractions with proteolytic activity from the Sephadex G25 column were combined and applied to a 150 ml CM Sepharose CL 6B cation exchange column (5 cm diameter) equilibrated with a buffer containing 0.01 M dimethylglutaric acid, 0.2 M boric acid, and 0.002 M calcium chloride adjusted to pH 6.5.

The protease was eluted using a linear gradient of 0–0.1 M sodium chloride in 2 liters of the same buffer.

In a final purification step, protease-containing fractions from the CM Sepharose column were combined and concentrated in an Amicon ultrafiltration cell equipped with a GR81PP membrane (from the Danish Sugar Factories Inc.).

By using the techniques mentioned above for the construction and fermentation, and the above isolation procedure, the novel subtilase having the amino acid sequence set forth in SEQ ID NO:2 was produced and isolated.

EXAMPLE 2

The "Model Detergent Wash Performance Test"

In order to asses the wash performance of subtilases in a standard detergent composition, standard washing experiments may be performed using the below experimental conditions:

| | |
|---|---|
| Detergent: | Model detergent |
| Detergent dosage | 4.0 g/l |
| pH | 10.1 |
| Wash time | 20 min |
| Temperature: | 30° C. |
| Water hardness: | 15° dH |
| Enzyme concentration: | 10 nm (in the detergent solution) |
| Test system: | 10 ml beakers with a stirring rod |
| Textile/volume: | 5 textile pieces (O 2.5 cm)/ 50 ml detergent solution |
| Test material: | WFK10N (egg stains) |

The composition of the model detergent is as follows:

6.2% LAS (Nansa 80S)
2% Sodium salt of $C_{16}$–$C_{18}$ fatty acid
4% Non-ionic surfactant (Plurafax LF404)
22% Zeolite P
10.5% $Na_2CO_3$
4% $Na_2Si_2O_5$
2% Carboxymethylcellulose (CMC)
6.8% Acrylate liquid CP5 40%
20% Sodium perborate (empirical formula $NaBO_2 \cdot H_2O_2$)
0.2% EDTA
21% $Na_2SO_4$
Water (balance)

pH of the detergent solution is adjusted to 10.1 by addition of HCl or NaOH. Water hardness is adjusted to 15° dH by addition of $CaCl_2$ and $MGCl_2$ ($Ca^{2+}$:$Mg^{2+}$=4:1) to the test system. After washing the textile pieces were flushed in tap water and air-dried.

Measurement of the reflectance ($R_{subtilase}$) on the test material is performed at 460 nm using a Macbeth ColorEye 7000 photometer (Macbeth, Division of Kollmorgen Instruments Corporation, Germany). The measurements are performed accordance with the manufacturer's protocol.

In order to determine a blank value, a similar wash experiment is performed without addition of enzyme. The subsequent measurement of the reflectance ($R_{blank}$) is performed as described right above.

A reference experiment is then performed as described above, wherein the wash performance of Savinase® is tested. The subsequent measurement of the reflectance ($R_{savinase}$) is performed as described right above.

The wash performance is evaluated by means of the Performance Factor (P) which is defined in accordance with the below formula:

$$P = (R_{subtilase} - R_{blank}) - (R_{savinase} - R_{blank})$$
$$= R_{subtilase} - R_{savinase}.$$

Using the above test method the following results were obtained:

| Enzyme | R (460 nm) | P |
|---|---|---|
| Blank (no enzyme) | 40.5 | — |
| Savinase ® | 40.7 | — |
| SEQ ID NO: 2 | 46.5 | 5.8 |

As it appears, the subtilase according to the invention exhibits improved wash performance on egg stains in comparison to Savinase".

EXAMPLE 3

Performance of the Subtilase of the Invention in Automatic Dishwashing (ADW)

The performance of the subtilase of the invention in ADW was tested in a commercial available household dishwash composition (Somat Turbo, from Henkel Washmittel GmbH) using standard conditions. The soil used was an egg/milk mixture coated on a steel plate. Further, a ballast soil containing various foodstuffs was added.

| | |
|---|---|
| Detergent: | Somat Turbo |
| Detergent dosage | 4.0 g/l |
| pH | 10.7 (as is) |
| Water hardness: | 3° dH (machine ion exchanger) |

-continued

| Temperature: | 55° C. |
| --- | --- |
| Enzyme concentration: | 20 nM and 40 nM, based on the total volume of wash water in the machine |
| Test method: | Egg/milk soiling on steel plates as described below |
| Machine: | Cylinda Compact |
| Wash program: | Program 4 without pre-flush |

Materials 220 ml full cream milk
15 eggs, medium size
Steel plates, diameter 18 cm
The Somat Turbo dishwash composition was heated at 85° C. for 5 minutes in a microwave oven in order to inactivate enzyme activity in the composition.

Soiling of Steel Plates 220 ml full cream milk was mixed with 15 raw eggs in a Braun UK
20 kitchen machine for 2 minutes, After sieving, stainless steel plates were soiled in the mixture by immersion.
The plates were dried overnight at room temperature in an upright position. The dried plates were then heated at 120° C. for 45 minutes in order to denature the proteins on the surface.

ADW Experiments

For each experiment, 10 soiled plates were washed without prewash (Program 4) in a Cylinda Compact machine. In addition to the soiled plates, the machine was filled up with 10 porcelain plates, 4 glasses, 4 cups and 16 pieces of cutlery.

Furthermore, 50 g of ballast slurry was added to the machine. The composition of the slurry was as follows:

Potato starch (5.43%), wheat flour (4.38%), vegetable oil (4.32%), margarine (4.32%), lard (4.32%), cream (8.76%), full cream milk (8.76%), eggs (8.76%), tomato ketchup (3.00%), barbecue sauce (2.19%), mustard (4.00%), benzoic acid (0.73%), water (3 mM $Ca^{2+}+Mg^{2+}$) (36.71%).

Measurements and Calculations

The light reflection values (R-values) were measured at six different locations on the plates using a Minolta Chroma Meter (Type: CR-300). Measurements were made on clean plates ($R_{clean}$), on soiled plates after heating ($R_{soiled}$) and on plates after wash ($R_{after\ wash}$).

The removed protein film (%RPF) was calculated according to the below formula:

$$\%RPF=100\%\times(R_{after\ wash}-R_{soiled})/(R_{clean}-R_{soiled})$$

Using the above test method the following results were obtained (± indicates the standard deviation):

| Enzyme | % RPF (20 nM) | % RPF (40 nm) |
| --- | --- | --- |
| Savinase ® | 3.9 ± 1.6 | 3.0 ± 1.0 |
| SEQ ID NO: 2 | 42.4 ± 16.5 | 78.7 ± 2.1 |

As it appears, the enzyme of the invention has a superior performance as compared to Savinase®.

DEPOSIT OF BIOLOGICAL MATERIAL

The following biological material has been deposited under the terms of the Budapest Treaty with the Deutsche Sammlung von Mikroorganismen und Zellkulturen GmbH, Mascheroder Weg 1 B, D-38124 Braunschweig, Germany, and given the following accession number:

| Deposit | Accession Number | Date of deposit |
| --- | --- | --- |
| E. coli MT173 | DSM 13306 | 10 Feb. 2000 |

What is claimed is:

1. A subtilase having an amino acid sequence which has at least 95% identity with the amino acid sequence of SEQ ID NO: 2.

2. The subtilase of claim 1, wherein the amino acid sequence has at least 96% identity with the amino acid sequence of SEQ ID NO: 2.

3. The subtilase of claim 1, wherein the amino acid sequence has at least 97% identity with the amino acid sequence of SEQ ID NO: 2.

4. The subtilase of claim 1, wherein the amino acid sequence has at least 98% identity with the amino acid sequence of SEQ ID NO: 2.

5. The subtilase of claim 1, wherein the amino acid sequence has at least 99% identity with the amino acid sequence of SEQ ID NO: 2.

6. The subtilase of claim 1, which comprises an amino acid sequence of SEQ ID NO: 2.

7. The subtilase of claim 1, which is encoded by a nucleic acid sequence which hybridizes under high stringency conditions with SEQ ID NO: 1 or its complementary strand, wherein the high stringency conditions are defined as prehybridization and hybridization at 42° C. in 5×SSPE, 0.3% SDS, 200 micrograms/ml sheared and denatured salmon sperm DNA, and 50% formamide, following Southern blotting procedures, followed by washing three times each for 15 minutes using 2×SSC, 0.2% SDS at a temperature of 65° C.

8. A modified subtilase comprising a mutation in an amino acid sequence of SEQ ID NO: 2, wherein the mutation is a substitution of at least one additional amino acid residue at one or more positions selected from the group consisting of modification in one of the positions 27, 36, 56, 76, 87, 97, 101, 104, 120, 123, 167, 170, 222, 224, 235 and 274 or an insertion at position 36, wherein the positions are numbered according to the amino acid sequence of the mature subtilisin BPN'.

9. A modified subtilase of claim 8, wherein the mutation is selected from the group consisting of K27R, *36D, S56P, N76D, S87N, G97N, R101G, S103A, V104A, V104I, V104N, V104Y, H120D, N123S, Y167X, R170X, M222A, M222S, T224S, K235L and T274A.

10. An isolated nucleic add sequence comprising a nucleic acid sequence which-encodes for a subtilase of claim 1.

11. A nucleic acid construct comprising the nucleic acid sequence of claim 10 operably linked to one or more control sequences capable of directing the expression of the subtilase in a suitable host.

12. An isolated nucleic acid sequence comprising a nucleic acid sequence which encodes for a modified subtilase of claim 8.

13. A nucleic acid construct comprising the nucleic acid sequence of claim 12 operably linked to one or more control sequences capable of directing the expression of the subtilase in a suitable host.

14. A recombinant expression vector comprising the nucleic acid construct of claim 11, a promoter, and transcriptional and translational stop signals.

15. A recombinant expression vector comprising the nucleic acid construct of claim 13, a promoter, and transcriptional and translational stop signals.

16. A recombinant host cell comprising the nucleic acid construct of claim 11.

17. A recombinant host cell comprising the nucleic acid construct of claim 13.

18. A method for producing a subtilase, comprising:

(a) cultivating a recombinant host cell of claim 16 under conditions conducive to the production of the subtilase; and (b) recovering the subtilase.

19. A method for producing a modified subtilase, comprising:

(a) cultivating a recombinant host cell of claim 17 under conditions conducive to the production of the modified subtilase; and (b) recovering the modified subtilase.

20. A cleaning or detergent composition, comprising the subtilase of claim 1 and a surfactant.

21. The composition of claim 20, which additionally comprises an amylase, cellulase, cutinase, lipase, oxidoreductase, another protease, or a mixture thereof.

22. A cleaning or detergent composition, comprising a modified subtilase of claim 8 and a surfactant.

23. A composition of claim 22, which additionally comprises an amylase, cellulase, cutinase, lipase, oxidoreductase, another protease, or a mixture thereof.

24. A method for cleaning or washing a hard surface or, laundry, comprising contacting the hard surface or the laundry with the composition of claim 20.

25. A method for cleaning or washing a hard surface or laundry, comprising contacting the hard surface or the laundry with the composition of claim 22.

* * * * *